(12) United States Patent
Norris et al.

(10) Patent No.: US 11,358,964 B2
(45) Date of Patent: Jun. 14, 2022

(54) METHODS OF TREATMENT USING BCN057 AND BCN512

(71) Applicant: BCN Biosciences L.L.C., Inglewood, CA (US)

(72) Inventors: Andrew J. Norris, Los Angeles, CA (US); Sudip Chakrabortty, San Jose, CA (US)

(73) Assignee: BCN Biosciences L.L.C., Inglewood, CA (US)

( * ) Notice: Subject to any disclaimer, the term of this patent is extended or adjusted under 35 U.S.C. 154(b) by 0 days.

(21) Appl. No.: 17/001,592

(22) Filed: Aug. 24, 2020

(65) Prior Publication Data

US 2021/0053968 A1 Feb. 25, 2021

Related U.S. Application Data

(60) Provisional application No. 62/891,338, filed on Aug. 24, 2019.

(51) Int. Cl.
*C07D 471/04* (2006.01)
*C07D 241/04* (2006.01)

(52) U.S. Cl.
CPC ......... *C07D 471/04* (2013.01); *C07D 241/04* (2013.01)

(58) Field of Classification Search
CPC .......................... C07D 471/04; C07D 241/04
See application file for complete search history.

(56) References Cited

U.S. PATENT DOCUMENTS 8,227,603 B2 * 7/2012 Russell ................ C07D 487/04
544/350

* cited by examiner

*Primary Examiner* — Timothy R Rozof
(74) *Attorney, Agent, or Firm* — Entralta P.C.; James F. Fleming; Peter D. Weinstein

(57) ABSTRACT

The present disclosure is directed to methods of treating or ameliorating various conditions by the administration of a BCN057, BCN512 or analogs of these compounds. The compounds can be used to reduce tumor burden in cancers, including pancreatic cancer and gastrointestinal (GI) cancer. The compounds can also be used to protect against chemotherapy induced toxicity to the GI tract. Further, they can be used to treat fibrosis and various inflammatory conditions. Analogs of BCN057 and BCN512 are also described.

8 Claims, 7 Drawing Sheets

Effects of 10uM BCN057 on the viability of pancreatic cancer cell lines
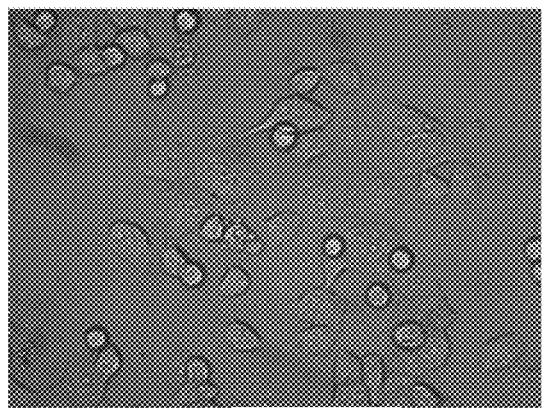
FIG. 3A    0 min.
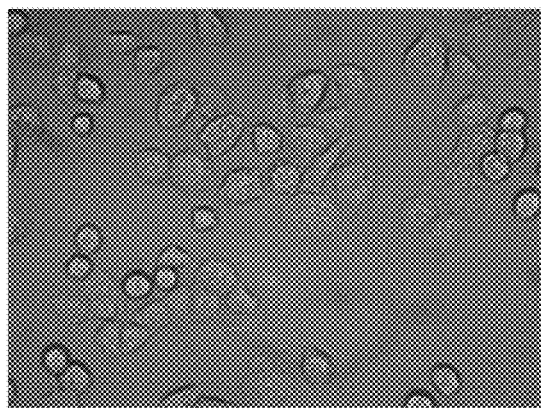
FIG. 3B    15 min.
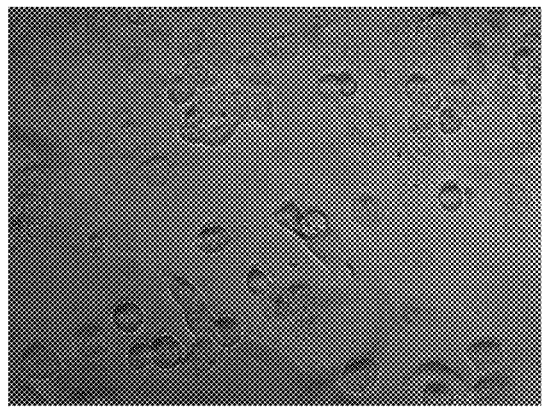
FIG. 3C    30 min.
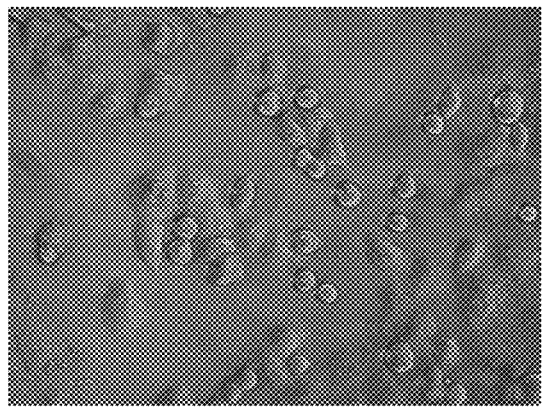
FIG. 3D    60 min.
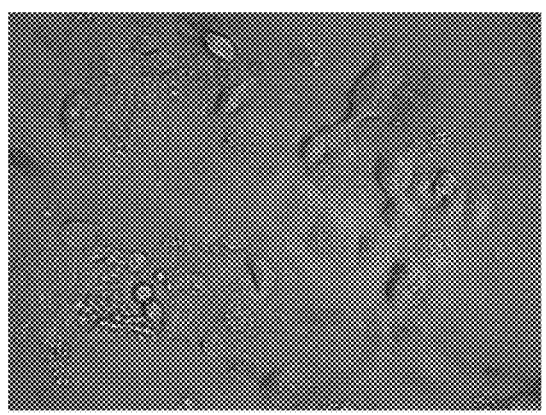
FIG. 3E    120 min.
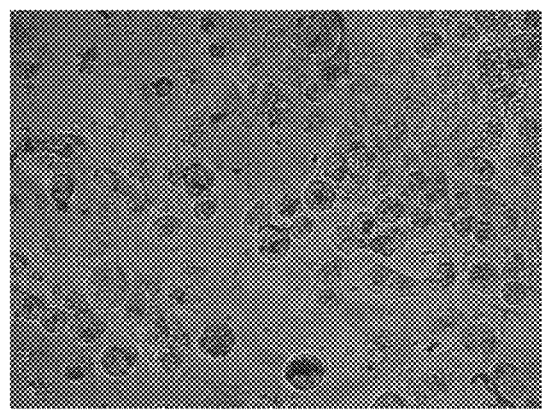
FIG. 3F    240 min.

|  | 0 | 24 hr | 48 hr | 72 hr |
|---|---|---|---|---|
| 10uM 057 | | 45.33834 | 32.39733 | 46.27488 |
| 10uM H | | 113.7799 | 89.10513 | 65.52249 |
| 10uM K | | 107.2702 | 79.2419 | 69.27018 |

Compound H

Compound K

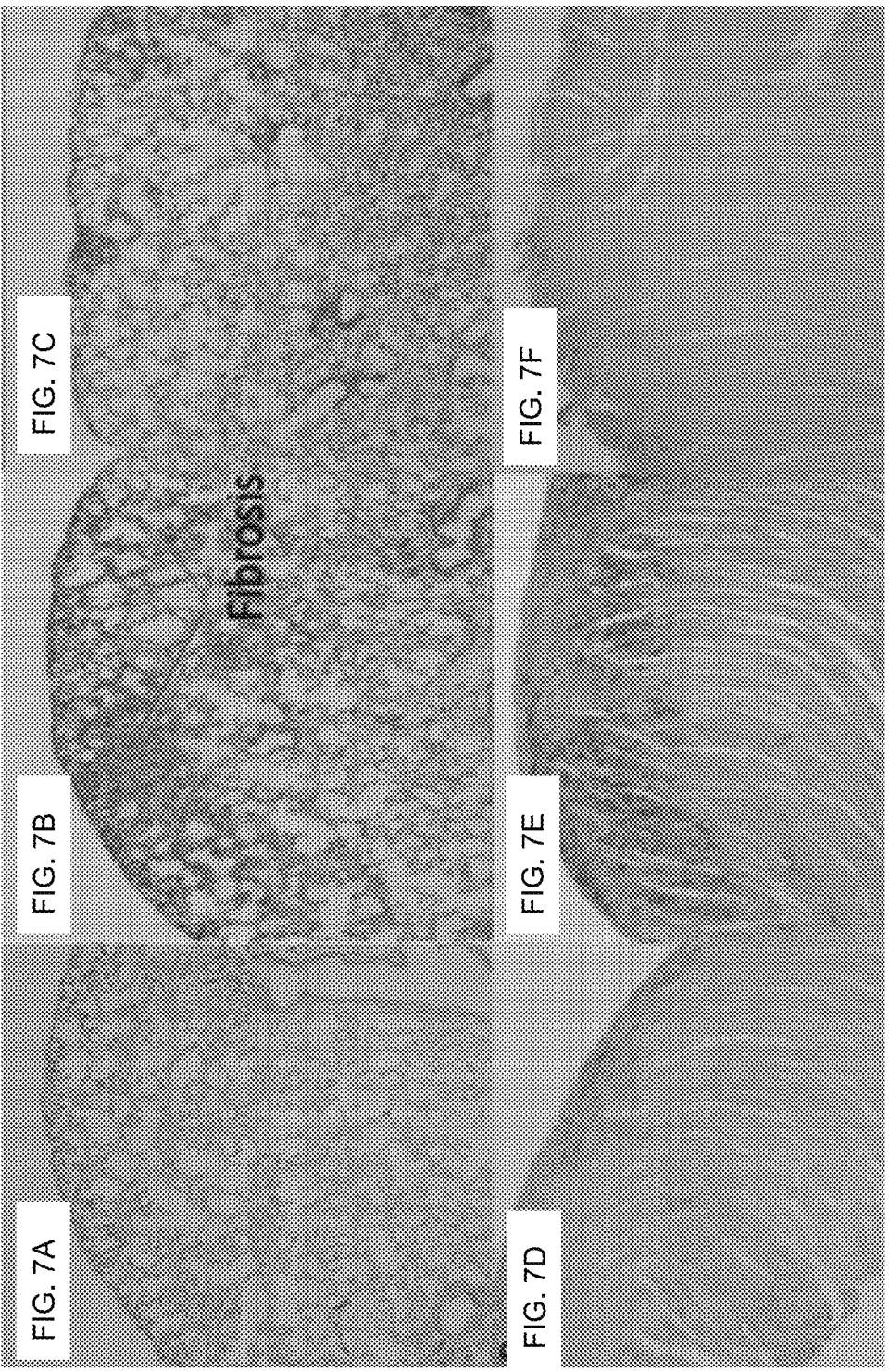

METHODS OF TREATMENT USING BCN057 AND BCN512

RELATED APPLICATIONS

This application claims priority to U.S. provisional patent application Ser. No. 62/891,338 filed on Aug. 24, 2019. The contents of the aforementioned application are incorporated herein by reference.

FIELD OF THE INVENTION

The invention relates novel small molecules and their therapeutic use, and more specifically, to therapeutic applications of the small molecules BCN057 and BCN512 and analogs thereof.

BACKGROUND

Cancer can be defined as a group of diseases that involve abnormal cell growth with the potential to invade or spread to other parts of the body. Despite advances in technology, cancer continues to be a significant cause of death and incalculable suffering. Cancer is the second most common cause of death in the United States.

Patients with cancer often have limited treatment options. Treatment can include a combination of surgery, radiation therapy, chemotherapy and targeted therapy. Despite advances in research, these treatments remained relatively unchanged in recent decades. Efforts have often focused on early diagnosis of cancer when treatments are more effective. However, the survival times afforded by early diagnosis are modest. Recent studies have provided new opportunities for cancer treatment, including the use of Wingless-type (Wnt) pathway modulators.

The Wnt signaling pathways are a group of signal transduction pathways which begin with proteins that pass signals into a cell through cell surface receptors. Aberrant activation of the Wnt pathway is implicated in human cancers, particularly those of the gastrointestinal (GI) tract. Inhibition of aberrant Wnt pathway activity in cancer cell lines can block their growth, presenting the possibility of new therapeutics. Alternatively, activation of Wnt signaling and its downstream genes in cancer may induce apoptosis in cancer cells.

The Wnt signaling pathway is often divided into two categories: the canonical and non-canonical pathways. The canonical pathway is typically referred to as the β-catenin-dependent pathway. The non-canonical pathway does not rely on β-catenin and is responsible for controlling cell movement during morphogenesis. While both pathways have been implicated in cancer development, the canonical pathway is most commonly recognized for its implications in gastrointestinal (GI) cancer.

There is a need for improved therapies that can be achieved with Wnt signal modulators. Modulators of Wnt/β-catenin signaling also have potential in treating other ailments, including fibrosis, inflammatory conditions, bone growth and alopecia. Accordingly, there is a need for compounds and methods that can inhibit and/or control Wnt/β-catenin signaling. Specifically, there is a need for an effective Wnt pathway modulator.

SUMMARY OF THE INVENTION

Compound BCN057 disclosed herein were previously described in U.S. patent application Ser. No. 13/813,923 and U.S. patent application Ser. No. 14/889,719. The present invention provides new analogs and new methods of use. BCN057 (also called YEL002), BCN512 and analogs of each compound are described below. The subject compounds are useful for, among other therapies, treating or preventing inflammatory disease and for treating or preventing cancer or other hyperproliferative conditions.

One embodiment is a compound of Formula A or an analog thereof,

Formula A

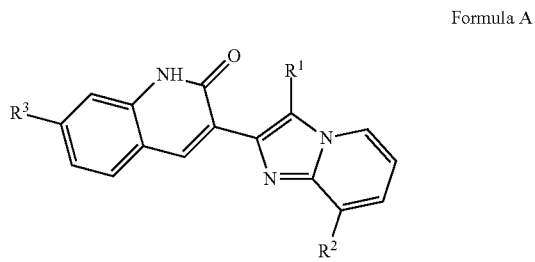

wherein $R^3$ is O—$CH_3$, $R^2$ is $CH_3$ or H and $R^1$ is one of:

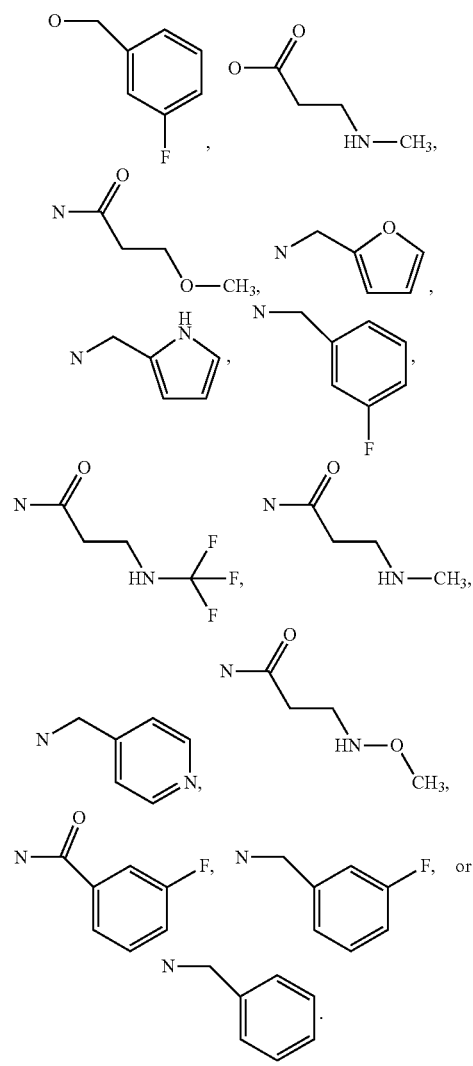

Another embodiment is a method of treating an ailment in a subject, comprising administering to the subject a therapeutically effective amount of a compound having the structure of Formula B:

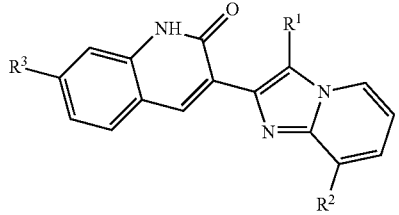

Formula B wherein:
R$^1$ is an alkyl, alkyl amine, or an ether;
R$^2$ is H or CH$_3$; and
R$^3$ is H or OH.

Analogs of Formula B can include Formula II, Formula III, Formula IV, Formula V, Formula VI, Formula VII, Formula VIII, Formula IX, Formula X, Formula XII, Formula XIII, Formula XIV, Formula XV, Formula XVI, Formula XVII, Formula XVIII and Formula XIX as described herein.

Additional embodiments include is a method of treating cancer in a subject with a therapeutically effective amount of a compound of Formula B or an analog thereof. The cancer can be bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, rectal cancer, skin cancer, blood cancer or testicular cancer. The treatment can include administering one or more additional medicaments to the subject as well as chemotherapy or radiotherapy.

Additional embodiments include a method of treating a subject with one or more side effects of chemotherapy or radiotherapy with the compound of Formula B or an analog thereof. Yet another embodiment is a method of preventing or treating radiation induced damage to epithelial cells by administering a therapeutically effective amount of a compound of Formula B or an analog thereof. The radiation induced damage to epithelial cells can be identified as radiation-induced gastrointestinal syndrome (RIGS), radiation-induced mucositis, radiation-induced oral mucositis, radiation-induced proctitis and/or radiation-induced enteritis.

Additional embodiments include a method of treating fibrosis with compound of Formula B or an analog thereof. The fibrosis can be pulmonary fibrosis, idiopathic pulmonary fibrosis, acute respiratory distress syndrome, cystic fibrosis, non-cystic fibrosis bronchiectasis, cirrhosis, liver fibrosis, endomyocardial fibrosis, old myocardial infarction, atrial fibrosis, mediastinal fibrosis, myelofibrosis, retroperitoneal fibrosis, progressive massive fibrosis, nephrogenic systemic fibrosis, Crohn's disease, gastrointestinal fibrosis, keloid conditions, scleroderma/systemic sclerosis, arthofibrosis, peyronie's disease, dupuytren's contracture, oral submucous fibrosis, liver fibrosis, gastrointestinal fibrosis, renal fibrosis from kidney dialysis and/or adhesive capsulitis.

Additional embodiments include a method of treating a viral infection in a subject in need thereof with a compound of Formula B or an analog thereof. Embodiments also include a method of treating depression with a compound of Formula B or an analog thereof.

In one aspect, disclosed herein, is a method of treating a subject with a therapeutically effective amount of the compound BCN057:

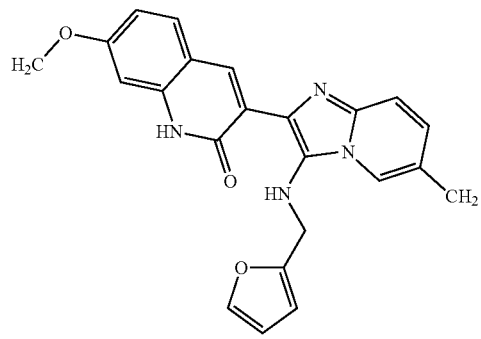

BCN057 can also be referred to by its structural name: (3-[(Furan-2-ylmethyl)-amino]-2-(7-methoxy-2-oxo-1,2-dihydro-quinolin-3-yl)-6-methyl-imidazo[1,2-a]pyridin-1-ium).

In another embodiment, the disclosure provides a method of treating cancer in a subject in need thereof, the method comprising the step of administering to the subject a therapeutically effective amount of a compound of BCN057, or an analog thereof. In another embodiment, the disclosure provides a method of treating cancer in a subject in need thereof, the method comprising the step of administering to the subject a combination of medicaments that includes a therapeutically effective amount of compound BCN057, or an analog thereof.

In another embodiment, the disclosure provides a method of treating side effects of chemotherapy or radiation therapy in a subject, the method comprising the step of administering to the subject a therapeutically effective amount of a compound of BCN057, or an analog thereof. In another embodiment, the disclosure provides a method of treating radiation-induced gastrointestinal syndrome (RIGS) in a subject, the method comprising administering to the subject a therapeutically effective amount of compound BCN057, or an analog thereof.

In one aspect, disclosed herein, is a method of treating a subject with a therapeutically effective amount of the compound BCN512. The structure of compound BCN512 is shown below and is also known as 1-[(4-nitrobenezene)sulfonyl]-4-phenyl piperazine. Analogs include BCN512A1 and BCN512B.

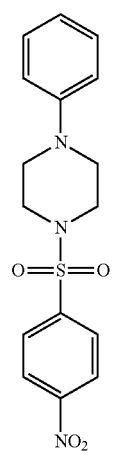

In another embodiment, the disclosure provides a method of modulating Wnt signaling in a subject, comprising administering a therapeutically effective amount of a compound of BCN512, or an analog thereof.

In another embodiment, the disclosure provides a method of treating a subject with fibrosis, the method comprising administering to the subject a combination of medicaments that includes a therapeutically effective amount of a compound of BCN512 or an analog thereof.

In another embodiment, the disclosure provides a method of inhibiting SFRP activity in a subject, the method comprising administering to the subject a therapeutically effective amount of a compound of BCN512 or an analog thereof.

In another embodiment, the disclosure provides a method of treating fibrosis in a subject in need thereof, the method comprising administering to the subject a therapeutically effective amount of a compound of BCN512 or an analog thereof. In another embodiment, the fibrotic disease is pulmonary fibrosis, idiopathic pulmonary fibrosis, acute respiratory distress syndrome, cystic fibrosis, non-cystic fibrosis bronchiectasis, cirrhosis, liver fibrosis (caused, for example by chronic viral hepatitis B or C), endomyocardial fibrosis, old myocardial infarction, atrial fibrosis, mediastinal fibrosis (soft tissue of the mediastinum), myelofibrosis (bone marrow), retroperitoneal fibrosis, progressive massive fibrosis, nephrogenic systemic fibrosis, Crohn's disease, gastrointestinal fibrosis, keloid conditions, scleroderma/systemic sclerosis, arthofibrosis, peyronie's disease, dupuytren's contracture, oral submucous fibrosis, or adhesive capsulitis.

In another embodiment, the disclosure provides a method of treating a disease of bone density or lack of bone density using BCN512 or an analog thereof. Examples include, osteoporosis, aging and lack of bone density, bone fracturing or breaking.

In another embodiment, the disclosure provides a method of treating the lack of hair growth or balding BCN512 or an analog thereof. Examples include alopecia, loss of hair due to age or patterned baldness.

In another embodiment, the invention provides compounds represented by Formula I or a pharmaceutically acceptable salt, ester, or prodrug thereof:

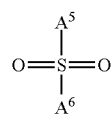

Formula Ia wherein:
A⁵ is a secondary or tertiary amine (i.e., thereby forming a sulfonamide), and
A⁶ is a substituted or unsubstituted aryl or heteroaryl group, preferably wherein the aryl or heteroaryl group bears at least one substituent including a nitro substituent, e.g., disposed at a position distal to the sulfonyl. In certain embodiments, A⁵ is a heterocyclic amine, such as a piperidine, piperazine, or morpholine ring, while in other embodiments, the amine is acyclic and/or the nitrogen atom bound to the sulfonyl is not included in any ring that may be present in A⁵.

Embodiments include a method of modulating Wnt activity to treat an ailment in a subject, comprising administering to the subject a therapeutically effective amount of a compound having the structure of Formula Ia. The ailment can be radiation exposure, fibrosis, insulin sensitivity, cancer, osteoporosis, alopecia/hair growth, wound healing, low bone density and/or obesity. The ailment can also be one or more side effects of chemotherapy or radiotherapy.

In another embodiment, the invention provides compounds represented by Formula II or a pharmaceutically acceptable salt, ester or prodrug thereof:

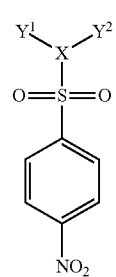

Formula IIa wherein:
X is N or —C(H)—, preferably N;
Y¹ and Y² are each independently lower alkyl or Y¹ and Y² taken together with X form a heterocyclyl ring system, such as

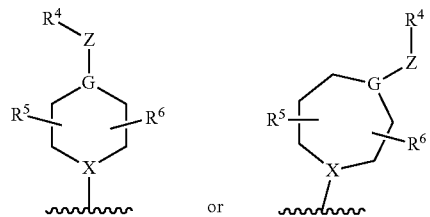

wherein
X is N, C or CH;
G is N, C or CH;
Z is absent or selected from substituted or unsubstituted alkyl, heteroalkyl, alkenyl, or alkynyl; and
R⁴ is hydrogen or selected from substituted or unsubstituted aryl (e.g., phenyl) and heteroaryl, and
R⁵ and R⁶ are each independently absent or lower alkyl.

In other embodiments, X, Y¹ and Y² taken together form a ring system

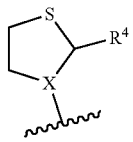

wherein X is —C(H)—, and
R⁴ is selected from substituted or unsubstituted aryl (e.g.; phenyl) and heteroaryl, such as a halogen-substituted phenyl group, e.g.; 4-fluorophenyl or 3-chlorophenyl.

In certain embodiments, Y¹ and Y² are each ethyl.
In certain preferred embodiments, Y¹ and Y² taken together form a piperazine ring.
In certain preferred embodiments; Z is absent.

Embodiments include a method of modulating Wnt activity to treat an ailment in a subject, comprising administering to the subject a therapeutically effective amount of a compound having the structure of Formula IIa. The ailment can be radiation exposure, fibrosis, insulin sensitivity, cancer, osteoporosis, alopecia/hair growth, wound healing, low bone density and obesity. The ailment can also be one or more side effects of chemotherapy or radiotherapy. The fibrosis can be identified as pulmonary fibrosis, idiopathic pulmonary fibrosis, acute respiratory distress syndrome, cystic fibrosis, non-cystic fibrosis bronchiectasis, cirrhosis, liver fibrosis, endomyocardial fibrosis, old myocardial infarction, atrial fibrosis, mediastinal fibrosis, myelofibrosis, retroperitoneal fibrosis, progressive massive fibrosis, nephrogenic systemic fibrosis, Crohn's disease, gastrointestinal fibrosis, keloid conditions, scleroderma/systemic sclerosis, arthofibrosis, peyronie's disease, dupuytren's contracture, oral submucous fibrosis, liver fibrosis, gastrointestinal fibrosis, renal fibrosis from kidney dialysis or adhesive capsulitis Another embodiment is a compound of Formula C or an analog thereof,

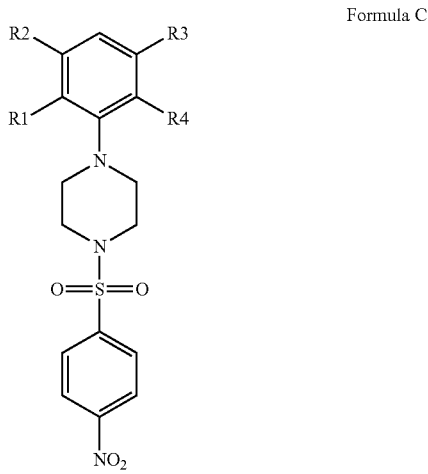

Formula C $R_1$ = a halogen, N, OH, $CH_3$, OH, $(CH_2)_n$—$CH_3$ or substituted or unsubstituted aryl;
$R_2$ = a halogen, N, OH, $CH_3$, OH, $(CH_2)_n$—$CH_3$ or substituted or unsubstituted aryl;
$R_3$ = a halogen, N, OH, $CH_3$, OH, $(CH_2)_n$—$CH_3$ or substituted or unsubstituted aryl;
$R_4$ = a halogen, N, OH, $CH_3$, OH, $(CH_2)_n$—$CH_3$ or substituted or unsubstituted aryl.
Analogs can include the compounds of Formula XXII, Formula)(XIII, Formula XXIV, Formula XXV, Formula XXVI and Formula)(XVII.

Embodiments also include a method of treating inflammation in a subject with a compound of Formula C or an analog thereof. The analog can be Formula)(XII, Formula XXIII, Formula XXIV, Formula XXV, Formula XXVI and/or Formula XXVII.

Embodiments also include a method of modulating Wnt activity to treat an ailment in a subject, comprising administering to the subject a therapeutically effective amount of a compound of Formula XXI or an analog thereof. The analog can be Formula XXII, Formula)(XIII, Formula)(XIV, Formula XXV, Formula XXVI and/or Formula XXVII. The ailment can be radiation exposure, fibrosis, insulin sensitivity, cancer, osteoporosis, alopecia/hair growth, wound healing, low bone density and/or obesity. The fibrosis can be pulmonary fibrosis, idiopathic pulmonary fibrosis, acute respiratory distress syndrome, cystic fibrosis, non-cystic fibrosis bronchiectasis, cirrhosis, liver fibrosis, endomyocardial fibrosis, old myocardial infarction, atrial fibrosis, mediastinal fibrosis, myelofibrosis, retroperitoneal fibrosis, progressive massive fibrosis, nephrogenic systemic fibrosis, Crohn's disease, gastrointestinal fibrosis, keloid conditions, scleroderma/systemic sclerosis, arthofibrosis, peyronie's disease, dupuytren's contracture, oral submucous fibrosis, liver fibrosis, gastrointestinal fibrosis, renal fibrosis from kidney dialysis or adhesive capsulitis.

In certain embodiments, compounds of the invention may be prodrugs of the compounds of formula I or II, e.g., wherein a hydroxyl in the parent compound is presented as an ester or a carbonate, or carboxylic acid present in the parent compound is presented as an ester. In certain such embodiments, the prodrug is metabolized to the active parent compound in vivo (e.g., the ester is hydrolyzed to the corresponding hydroxyl, or carboxylic acid).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. In certain embodiments, compounds of the invention may have more than one stereocenter. In certain such embodiments, compounds of the invention may be enriched in one or more diastereomer. For example, a compound of the invention may have greater than 30% de, 40% de, 50% de, 60% de, 70% de, 80% de, 90% de, or even 95% or greater de.

In certain embodiments, the present invention relates to methods of treatment with a compound of formula Ia, IIa, A, B, C, an analog and/or a pharmaceutically acceptable salt thereof. In certain embodiments, the therapeutic preparation may be enriched to provide predominantly one enantiomer of a compound (e.g., of formula Ia, IIa, A, B or C).

In certain embodiments, the therapeutic preparation may be enriched to provide predominantly one diastereomer of a compound (e.g., of formula Ia, IIa, A, B or C). A diastereomerically enriched mixture may comprise, for example, at least 60 mol percent of one diastereomer, or more preferably at least 75, 90, 95, or even 99 mol percent.

In certain embodiments, the present invention relates to methods of treatment with a compound of formula Formula Ia, IIa, A, B or C, or a pharmaceutically acceptable salt thereof. In certain embodiments, the therapeutic preparation may be enriched to provide predominantly one enantiomer of a compound (e.g., of formula Ia, IIa, A, B or C).

In certain embodiments, the therapeutic preparation may be enriched to provide predominantly one diastereomer of a compound (e.g., of formula Formula Ia, IIa, A, B or C). In certain embodiments, the present invention provides a pharmaceutical preparation suitable for use in a human patient, comprising any of the compounds shown above (e.g., a compound of the invention, such as a compound of Formula Ia, IIa, A, B or C), and one or more pharmaceutically acceptable excipients. In certain embodiments, the pharmaceutical preparations may be for use in treating or preventing a condition or disease as described herein, in certain embodiments, the pharmaceutical preparations have a low enough pyrogen activity to be suitable for use in a human patient. Compounds of any of the above structures may be used in the manufacture of medicaments for the treatment of any diseases or conditions disclosed herein.

Various other objects, features and attendant advantages of the present invention will become fully appreciated as the same becomes better understood when considered in conjunction with the accompanying drawings, in which like reference characters designate the same or similar parts throughout the several views, and wherein:

BRIEF DESCRIPTION OF THE FIGURES

FIG. 3A-3F show the effects of 10 uM BCN057 on the viability of pancreatic cancer cell lines. FIG. 3A shows pancreatic cancer cell lines at time 0; FIG. 3B at 15 minutes; FIG. 3C at 30 minutes; FIG. 3D at 60 minutes; FIG. 3E at 120 minutes; FIG. 3F at and 240 minutes.

FIG. 7A-7F show the histopathology of lung sections stained for TGFβ in C57M Male mice receiving nothing (A), 14Gy thoracic radiation (B) or radiation and BCNB512 (C). Images D, E and F are cardiac muscle stains under the same parameters from the same animals.

DEFINITIONS

Figure 1:
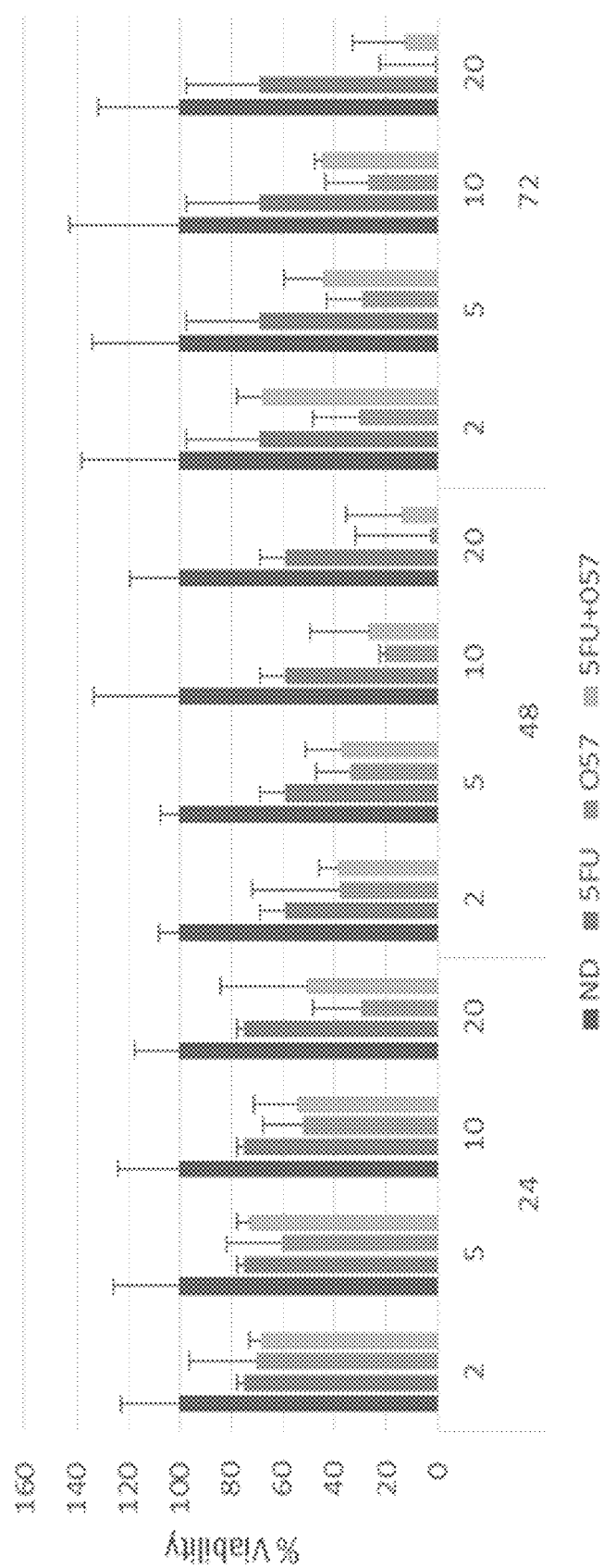
FIG. 1 shows the effects of 5-FU and BCN057 on the viability of pancreatic cancer cell lines.

Reference in this specification to "one embodiment/aspect" or "an embodiment/aspect" means that a particular feature, structure, or characteristic described in connection with the embodiment/aspect is included in at least one embodiment/aspect of the disclosure. The use of the phrase "in one embodiment/aspect" or "in another embodiment/aspect" in various places in the specification are not necessarily all referring to the same embodiment/aspect, nor are separate or alternative embodiments/aspects mutually exclusive of other embodiments/aspects. Moreover, various features are described which may be exhibited by some embodiments/aspects and not by others. Similarly, various requirements are described which may be requirements for some embodiments/aspects but not other embodiments/aspects. Embodiment and aspect can be in certain instances be used interchangeably.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present disclosure (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present disclosure and does not pose a limitation on the scope of the disclosure otherwise claimed. No language in the present specification should be construed as indicating any non-claimed element essential to the practice of the disclosure.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

As applicable, the terms "about" or "generally", as used herein in the specification and appended claims, and unless otherwise indicated, means a margin of +/−20%. Also, as applicable, the term "substantially" as used herein in the specification and appended claims, unless otherwise indicated, means a margin of +/−10%. It is to be appreciated that not all uses of the above terms are quantifiable such that the referenced ranges can be applied.

The term "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed. An active agent can be a primary active agent, or in other words, the component(s) of a composition to which the whole or part of the effect of the composition is attributed. An active agent can be a secondary agent, or in other words, the component(s) of a composition to which an additional part and/or other effect of the composition is attributed.

The term "cancer" can include one or more of Adenoid Cystic Carcinoma, Adrenal Gland Cancer, Amyloidosis, Anal Cancer, Ataxia-Telangiectasia, Atypical Mole Syndrome, Basal Cell Carcinoma, Bile Duct Cancer, Birt Hogg Dube Syndrome, Bladder Cancer, Bone Cancer, Brain Tumor, Breast Cancer, Breast Cancer in Men, Carcinoid Tumor, Cervical Cancer, Colorectal Cancer, Ductal Carcinoma, Endometrial Cancer, Esophageal Cancer, Gastric Cancer, Gastrontestinal Stromal Tumor (GIST), HER2-Positive Breast Cancer, Islet Cell Tumor, Juvenile Polyposis Syndrome, Kidney Cancer, Laryngeal Cancer, Leukemia—Acute Lymphoblastic Leukemia, Leukemia—Acute Lymphocytic (ALL), Leukemia—Acute Myeloid AML, Leukemia—Adult, Leukemia Childhood, Leukemia—Chronic Lymphocytic—CLL, Leukemia—Chronic Myeloid—CML, Liver Cancer, Lobular Carcinoma, Lung Cancer, Lung Cancer—Small Cell, Lymphoma—Hodgkin's, Lymphoma—Non-Hodgkin's, Malignant Glioma, Melanoma, Meningioma, Multiple Myeloma, Myelodysplastic Syndrome (MDS), Nasopharyngeal Cancer, Neuroendocrine Tumor, Oral Cancer, Osteosarcoma, Ovarian Cancer, Pancreatic Cancer, Pancreatic Neuroendocrine Tumors, Parathyroid Cancer, Penile Cancer, Peritoneal Cancer, Peutz-Jeghers Syndrome, Pituitary Gland Tumor, Polycythemia Vera, Prostate Cancer, Renal Cell Carcinoma, Retinoblastoma, Salivary Gland Cancer, Sarcoma, Sarcoma-Kaposi, Skin Cancer, Small Intestine Cancer, Stomach Cancer, Testicular Cancer, Thymoma, Thyroid Cancer, Uterine (Endometrial) Cancer, Vaginal Cancer and Wilms' Tumor. The term "blood cancer" can include one or more of leukemia, lymphoma, myeloma, myelodysplastic syndromes and myeloproliferative neoplasms.

The term "derivative" can refer to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. Derivatives can also include the salt forms, such as pharmaceutically acceptable salt forms of a parent compound or derivative thereof.

The term "fibrosis" refers to a condition with the formation of excess fibrous connective tissue in an organ or tissue in a reparative or reactive process. This can be a reactive, benign, or pathological state.

As used herein, "mitigating" means reducing one or more negative symptoms of a condition, relative to a cell, organ, tissue, or organism displaying the symptom or condition for the same amount of time, but untreated.

In some embodiments, contacting the cell, organ, tissue, or organism the present compounds may comprise administering a therapeutically effective amount of the compound to a subject. As used herein, a "therapeutically effective amount" is an amount sufficient to mitigate the negative symptom or condition.

The term "subject" or "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the present disclosure. A discussion is provided in Higuchi et al., "Prodrugs as Novel Delivery Systems," ACS Symposium Series, Vol. 14, and in Roche, E. B., ed. Bioreversible Carriers in Drug Design, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The term "chemotherapy" refers to a type of cancer treatment that uses one or more anti-cancer drugs (i.e. chemotherapeutic agents). Chemotherapy can be given with a curative intent (typically with combinations of drugs), or it can be used to prolong life or to reduce symptoms (i.e. palliative chemotherapy). Conventional chemotherapeutic agents are cytotoxic by means of interfering with cell division (mitosis). Common side effects of chemotherapy include myelosuppression, mucositis (inflammation of the lining of the digestive tract) and alopecia.

The term "KRAS" refers to a gene that acts as an "on/off" switch in cell signaling. When it functions normally, it controls cell proliferation. It can be allosterically activated and recruits and activates proteins necessary for the propagation of growth factors, along with other cell signaling receptors such as c-Raf and PI 3-kinase. Negative signaling can be disrupted when it is mutated causing cells to overproliferate and develop into cancer.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing, isolating, purifying, synthesizing, and recombinantly manufacturing) polypeptides are well known to one of ordinary skill in the art.

The term "RIGS" or "radiation-induced gastrointestinal syndrome" results from a combination of direct cytocidal effects of irradiation on intestinal crypt cells and stromal cells with loss of the mucosal barrier and symptoms ranging from diarrhea, electrolyte imbalance, weight loss and death. A significant proportion of patients experience radiation-induced toxicity due to damage to normal tissue in the irradiation field. The use of chemical or biological approaches aimed at reducing or preventing normal tissue toxicity induced by radiotherapy is a long-held goal.

The term "radiation therapy" or "radio therapy" refers to a therapy using ionizing radiation, generally as part of cancer treatment to control or kill malignant cells. Radiation therapy is commonly applied to the cancerous tumor because of its ability to control cell growth. Ionizing radiation works by damaging the DNA of cancerous tissue leading to cellular death. The main side effects are fatigue and skin irritation. Acute side effects can include nausea and vomiting, damage to the epithelial surfaces, mouth, throat and stomach sores, swelling, intestinal discomfort. RIGS (radiation induced gastrointestinal syndrome) is a common term used to describe side effect related to the gastrointestinal system.

The term "SFRP" or "secreted frizzled-related protein" refers to a Wnt signaling pathway inhibitor which is part of the soluble frizzled-related proteins (sFRPS). sFRPS function as modulators of Wnt signaling through direct interaction with Wnts. Five mammalian sFRPs have been identified (sFRP-1, sFRP-2, sFRP-3, sFRP-4 and sFRP-5). These proteins consist of approximately 300 amino acids containing a signal sequence, a Frizzled-like cysteine-rich domain (CRD), and a small hydrophilic C-terminal domain. As a group, sFRPs are expressed in a variety of embryonic and adult tissues, suggesting a common mechanism for inhibiting Wnt signaling. Individual family members, however, have specific spatial and temporal expression patterns.

The term "Wnt signaling pathways" refers to a group of signal transduction pathways which begin with proteins that pass signals into a cell through cell surface receptors. The canonical Wnt pathway leads to regulation of gene transcription.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. Treatment can be prophylactic and/or therapeutic. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

The term "TOPFLASH" or "TCF/LEF reporter kit" refers to a kit for monitoring the activity of Wnt/β-catenin signaling pathway in the cultured cells. The kit typically includes a TCF/LEF luciferase reporter vector which is a Wnt pathway-responsive reporter.

The term "unit dosage form" or "unit" as used herein refers to physically discrete units suitable as unitary dosages for human and animal subjects, each unit containing a predetermined quantity of the compound calculated in an amount sufficient to produce the desired effect in association with a pharmaceutically acceptable, diluent, carrier or vehicle. The specifications for the novel unit dosage forms of the present disclosure depend on the particular compound employed and the effect to be achieved, and the pharmacodynamics associated with each compound in the subject.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

The term "alkoxy" represents a chemical substituent of formula —OR, where R is an optionally substituted $C_1$-$C_6$ alkyl group, unless otherwise specified. In some embodiments, the alkyl group can be substituted, e.g., the alkoxy group can have 1, 2, 3, 4, 5 or 6 substituent groups as defined herein.

The term "alkoxyalkyl" represents a heteroalkyl group, as defined herein, that is described as an alkyl group that is substituted with an alkoxy group. Exemplary unsubstituted alkoxyalkyl groups include between 2 to 12 carbons. In some embodiments, the alkyl and the alkoxy each can be further substituted with 1, 2, 3, or 4 substituent groups as defined herein for the respective group.

The terms "alkyl," "alkenyl" and "alkynyl" include straight-chain, branched-chain and cyclic monovalent substituents, as well as combinations of these, containing only C and H when unsubstituted. Examples include methyl, ethyl, isobutyl, cyclohexyl, cyclopentylethyl, 2-propenyl, 3-butynyl, and the like. The term "cycloalkyl," as used herein, represents a monovalent saturated or unsaturated non-aromatic cyclic alkyl group having between three to nine carbons (e.g., a C3-C9 cycloalkyl), unless otherwise specified, and is exemplified by cyclopropyl, cyclobutyl, cyclopentyl, cyclohexyl, cycloheptyl, bicyclo[2.2.1.]heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. Typically, the alkyl, alkenyl and alkynyl groups contain 1-12 carbons (e.g., $C_1$-$C_{12}$ alkyl) or 2-12 carbons (e.g., $C_2$-$C_{12}$ alkenyl or $C_2$-$C_{12}$ alkynyl). In some embodiments, the alkyl groups are $C_1$-$C_8$, $C_1$-$C_6$, $C_1$-$C_4$, $C_1$-$C_3$, or $C_1$-$C_2$ alkyl groups; or $C_2$-$C_8$, $C_2$-$C_6$, $C_2$-$C_4$, or $C_2$-$C_3$ alkenyl or alkynyl groups. Further, any hydrogen atom on one of these groups can be replaced with a substituent as described herein.

Heteroalkyl, heteroalkenyl and heteroalkynyl are similarly defined and contain at least one carbon atom but also contain one or more O, S or N heteroatoms or combinations thereof within the backbone residue whereby each heteroatom in the heteroalkyl, heteroalkenyl or heteroalkynyl group replaces one carbon atom of the alkyl, alkenyl or alkynyl group to which the heteroform corresponds. In some embodiments, the heteroalkyl, heteroalkenyl and heteroalkynyl groups have C at each terminus to which the group is attached to other groups, and the heteroatom(s) present are not located at a terminal position. As is understood in the art, these heteroforms do not contain more than three contiguous heteroatoms. In some embodiments, the heteroatom is O or N. The term "heterocyclyl," as used herein represents cyclic heteroalkyl or heteroalkenyl that is, e.g., a 3-, 4-, 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopenlane ring, a cyclopentene ring, or another monocyclic heterocyclic ring, such as indolyl, quinolyl, isoquinolyl, tetrahydroquinolyl, benzofuryl, benzothienyl and the like.

The term "alkylsulfonyl," as used herein, represents a heteroalkyl group that is described as an optionally substituted alkyl group, as described herein, that includes an —S(O)$_2$— group.

The term "amino," as used herein, represents —N(R)$_2$, wherein each R is, independently, H, OH, NO$_2$, N(R)$_2$, SO$_2$OR, SO$_2$R, SOR, SO$_2$N(R)$_2$, SON(R)$_2$, an N-protecting group, alkyl, alkenyl, alkynyl, alkoxy, aryl, alkaryl, cycloalkyl, alkcycloalkyl, heterocyclyl (e.g., heteroaryl), alkheterocyclyl (e.g., alkheteroaryl), or two R combine to form a heterocyclyl or an N-protecting group, and wherein each $R^{N2}$ is, independently, H, alkyl, or aryl. In a preferred embodiment, amino is —NH$_2$, or —NHR, wherein R is, independently, OH, NO$_2$, NH$_2$, NR$_2$, SO$_2$OR, SO$_2$R, SOR, SO$_2$N(R)$_2$, SON(R)$_2$, alkyl, or aryl, and each R can be H, alkyl, or aryl. The term "aminoalkyl," as used herein, represents a heteroalkyl group, as defined herein, that is described as an alkyl group, as defined herein, substituted by an amino group, as defined herein. The alkyl and amino each can be further substituted with 1, 2, 3, or 4 substituent groups as described herein for the respective group. For example, the alkyl moiety may comprise an oxo (═O) substituent.

"Aromatic" moiety or "aryl" moiety refers to any monocyclic or fused ring bicyclic system which has the characteristics of aromaticity in terms of electron distribution throughout the ring system and includes a monocyclic or fused bicyclic moiety such as phenyl or naphthyl; "heteroaromatic" or "heteroaryl" also refers to such monocyclic or fused bicyclic ring systems containing one or more heteroatoms selected from O, S and N. The inclusion of a heteroatom permits inclusion of 5-membered rings to be considered aromatic as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, isoxazolyl, benzoxazolyl, benzoisoxazolyl, imidazolyl and the like. Because tautomers are theoretically possible, phthalimido is also considered aromatic. Typically, the ring systems contain 5-12 ring member atoms or 6-10 ring member atoms. In some embodiments, the aromatic or heteroaromatic moiety is a 6-membered aromatic rings system optionally containing 1-2 nitrogen atoms. More particularly, the moiety is an optionally substituted phenyl, pyridyl, indolyl, pyrimidyl, pyridazinyl, benzothiazolyl or benzimidazolyl, pyrazolyl, imidazolyl, isoxazolyl, thiazolyl, benzothiazolyl, indolyl. Even more particularly, such moiety is phenyl, pyridyl, or pyrimidyl and even more particularly, it is phenyl. "O-aryl" or "O-heteroaryl" refers to aromatic or heteroaromatic systems which are coupled to another residue through an oxygen atom. A typical example of an O-aryl is phenoxy. Similarly, "arylalkyl" refers to aromatic and heteroaromatic systems which are coupled to another residue through a carbon chain, saturated or unsaturated, typically of $C_1$-$C_2$, $C_1$-$C_6$, or more particularly $C_1$-$C_4$ or $C_1$-$C_3$ when saturated or $C_2$-$C_8$, $C_2$-$C_6$, $C_2$-$C_4$, or $C_2$-$C_3$ when unsaturated, including the heteroforms thereof. For greater certainty, arylalkyl thus includes an aryl or heteroaryl group as defined above connected to an alkyl, heteroalkyl, alkenyl, heteroalkenyl, alkynyl or heteroalkynyl moiety also as defined above. Typical arylalkyls would be an aryl($C_6$-$C_{12}$)alkyl($C_1$-$C_8$), aryl($C_6$-$C_{12}$)alkenyl ($C_2$-$C_8$), or aryl($C_6$-$C_{12}$)alkynyl($C_2$-$C_8$), plus the heteroforms. A typical example is phenylmethyl, commonly referred to as benzyl.

Halo may be any halogen atom, especially F, Cl, Br, or I, and more particularly it is fluoro or chloro.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls. In some embodiments, the haloalkyl group can be further substituted with 1, 2, 3, or 4 substituent groups as described herein for alkyl groups.

The term "hydroxy," as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like.

In general, a substituent group (e.g., alkyl, alkenyl, alkynyl, or aryl (including all heteroforms defined above) may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. For example, where a group is substituted, the group may be substituted with 1, 2, 3, 4, 5, or 6 substituents. Optional substituents include, but are not limited to: $C_1$-$C_6$ alkyl or heteroaryl, $C_2$-$C_6$ alkenyl or heteroalkenyl, $C_2$-$C_6$ alkynyl or heteroalkynyl, halogen; aryl, heteroaryl, azido (—N$_3$), nitro (—NO$_2$), cyano (—CN), acyloxy (—OC(═O)R'), acyl (—C(═O)R'), alkoxy (—OR'), amido (—NR'C(═O)R" or —C(═O) NR'R"), amino (—NR'R"), carboxylic acid (—CO$_2$H), carboxylic ester (—CO$_2$R'), carbamoyl (—OC(═O)NR'R" or —NRC(═O)OR'), hydroxy (—OH), isocyano (—NC), sulfonate (—S(═OHOR), sulfonamide (—S(═OHNRR' or —NRS(=O)$_2$R'), or sulfonyl (—S(=O)$_2$R), where each R or R' is selected, independently, from H, C$_1$-C$_6$ alkyl or heteroaryl, C$_2$-C$_6$ alkenyl or heteroalkenyl, C$_2$-C$_6$ alkynyl or heteroalkynyl, aryl, or heteroaryl. A substituted group may have, for example, 1, 2, 3, 4, 5, 6, 7, 8, or 9 substituents.

Typical optional substituents include independently halo, CN, NO$_2$, CF$_3$, OCF$_3$, COOR, CONR$^Y_2$, OR, SR, SOR, SO$_2$R, NR$_2$, NR(CO)R, NRC(O)OR, NRC(O)NR$_2$, NRSO$_2$NR$_2$, or NRSO$_2$R, wherein each R is independently H or an optionally substituted group selected from alkyl, alkenyl, alkynyl, heteroalkyl, heteroalkenyl, heteroalkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl and arylalkyl.

Other technical terms used herein have their ordinary meaning in the art that they are used, as exemplified by a variety of technical dictionaries. The particular values and configurations discussed in these non-limiting examples can be varied and are cited merely to illustrate at least one embodiment and are not intended to limit the scope thereof.

DETAILED DESCRIPTION

It is to be understood that both the foregoing general description and the following detailed description are exemplary and explanatory and are intended to provide further explanation of the subject technology as claimed. Additional features and advantages of the subject technology are set forth in the description below, and in part will be apparent from the description, or may be learned by practice of the subject technology. The advantages of the subject technology will be realized and attained by the structure particularly pointed out in the written description and claims hereof.

BCN057 and Analogs

BCN057, also known as YEL002, is represented by the following structure:

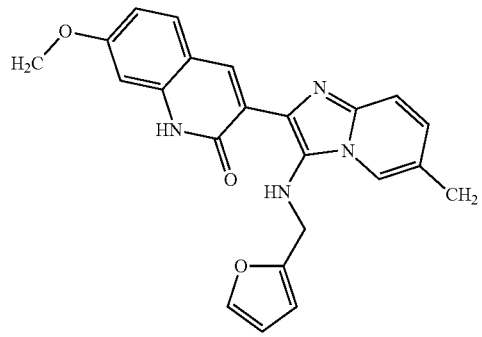

Formula I

It can also be described as (3-[(Furan-2-ylmethyl)-amino]-2-(7-methoxy-2-oxo-1,2-dihydro-quinolin-3-yl)-6-methyl-imidazo[1,2-a]pyridin-1-ium). It will be appreciated that the invention covers compounds of BCN057, analogues and salts thereof. In one embodiment, the invention relates to compounds of BCN057 in the form of a free base. In another embodiment, the invention relates to compounds of BCN057 or a pharmaceutically acceptable salt thereof.

Because of their potential use in medicine, salts of the compound of BCN057 may be preferred as pharmaceutically acceptable salts. Suitable pharmaceutically acceptable salts can include acid addition salts. A pharmaceutically acceptable salt can be readily prepared by using a desired acid or base as appropriate. The resultant salt can precipitate from solution and be collected by filtration or recovered by evaporation of the solvent. The compound can exist as a stereoisomer, tautomer, pharmaceutical acceptable salt, or hydrate thereof. Some analogs of BCN057 are presented below.

Embodiments include methods of treatment that include administering a therapeutically effective amount of a compound having the structure of Formula B:

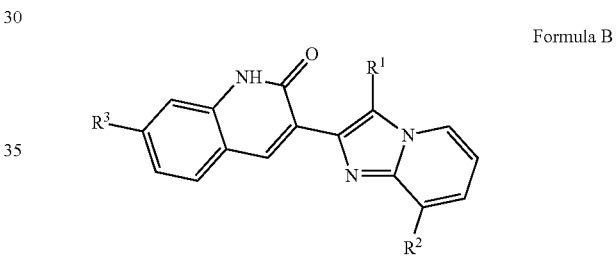

Formula B wherein:

R$^1$ is an alkyl, alkyl amine, or an ether;

R$^2$ is H or CH$_3$; and

R$^3$ is H or OH.

In some embodiments, the compound is an analog selected from Formula II-XIX, including Compound H, Compound K, Compound BNB-1, Compound BNB-2, Compound BNB-3, Compound BNB-4 and Compound BNB-5.

| BCN057 (Formula I) Analogs | Name |
|---|---|
| 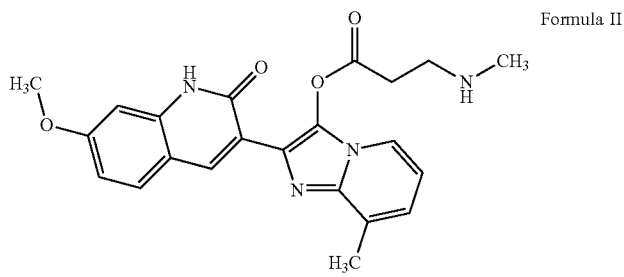 | Formula II |

-continued
| BCN057 (Formula I) Analogs | Name |
|---|---|
| 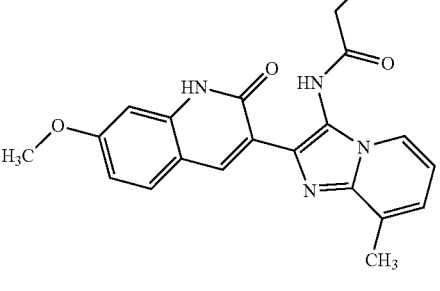 | Formula III |
| 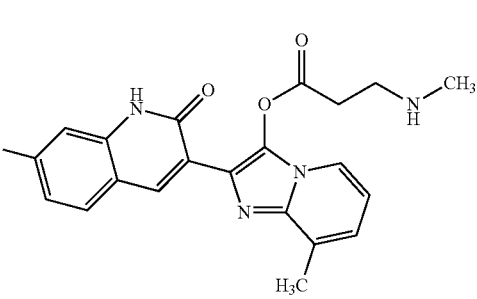 | Formula IV |
| 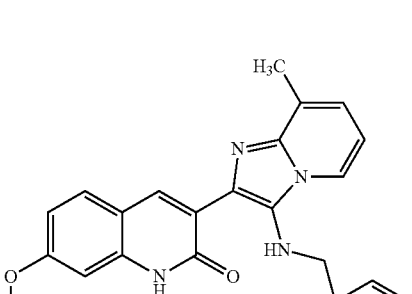 | Formula V |
| 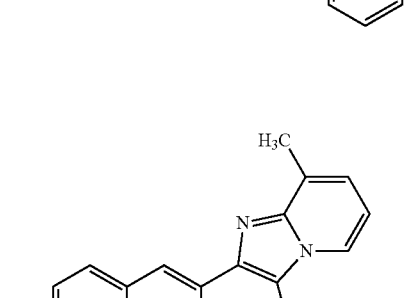 | Formula VI |

| BCN057 (Formula I) Analogs | Name |
|---|---|
| 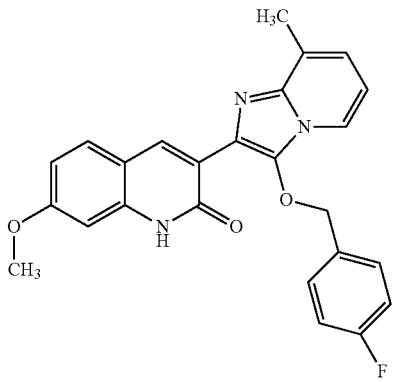 [SMILES: COc1ccc2cc(-c3nc4c(C)cccn4c3OCc3ccc(F)cc3)c(=O)[nH]c2c1] | Formula VII |
| 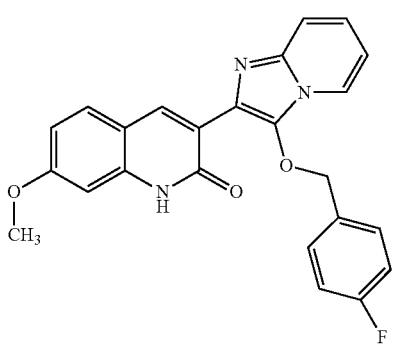 [SMILES: COc1ccc2cc(-c3nc4ccccn4c3OCc3ccc(F)cc3)c(=O)[nH]c2c1] | Formula VIII |
| 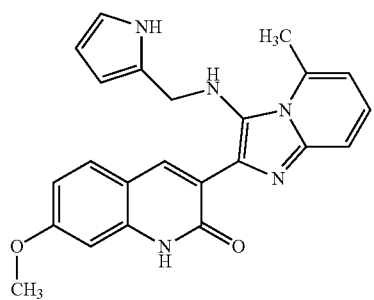 [SMILES: COc1ccc2cc(-c3nc4cccc(C)n4c3NCc3ccc[nH]3)c(=O)[nH]c2c1] | Formula IX |
| 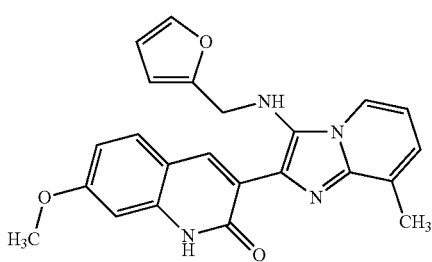 [SMILES: COc1ccc2cc(-c3nc4c(C)cccn4c3NCc3ccco3)c(=O)[nH]c2c1] | Formula X |

-continued
| BCN057 (Formula I) Analogs | Name |
|---|---|
| 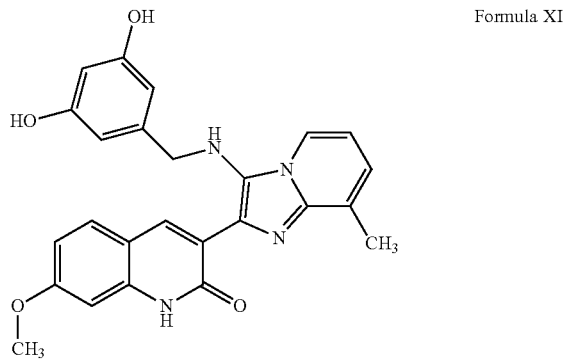 | Formula XI |
| 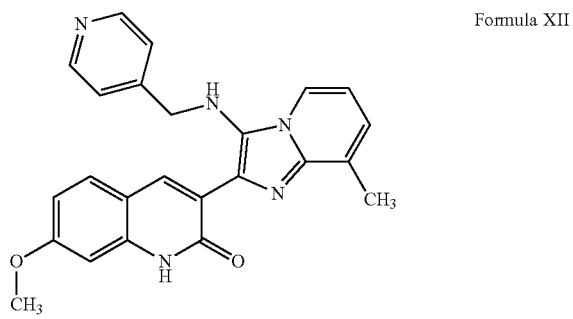 | Formula XII |
| 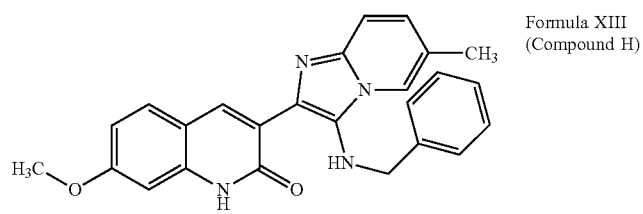 | Formula XIII (Compound H) |
| 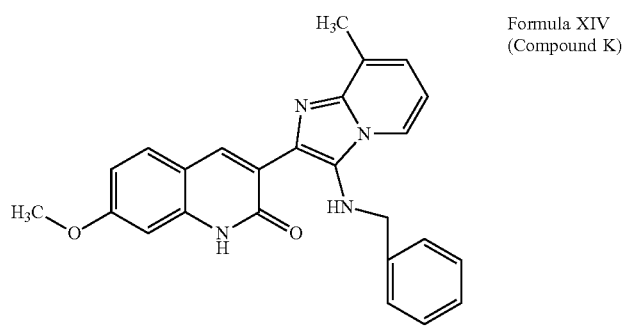 | Formula XIV (Compound K) |

| BCN057 (Formula I) Analogs | Name |
|---|---|
| | Formula XV (Compound BNB-1) |
| | Formula XVI (Compound BNB-2) |
| | Formula XVII (Compound BNB-3) |
| | Formula XVIII (Compound BNB-4) |

| BCN057 (Formula I) Analogs | Name |
|---|---|
| 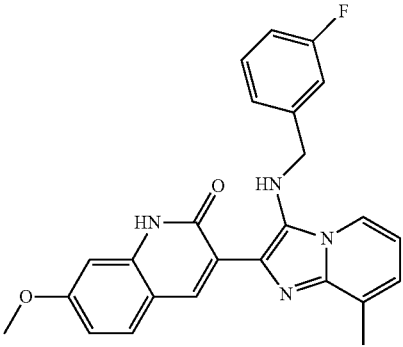 [SMILES: COc1ccc2cc(-c3nc4c(C)cccn4c3NCc3cccc(F)c3)c(=O)[nH]c2c1] | Formula XIX (Compound BNB-5) |
BCN512 and Analogs
The structure of compound BCN512 is shown below as Formula XXI, also known as 1-[(4-nitrobenezene)sulfonyl]-4-phenyl piperazine.
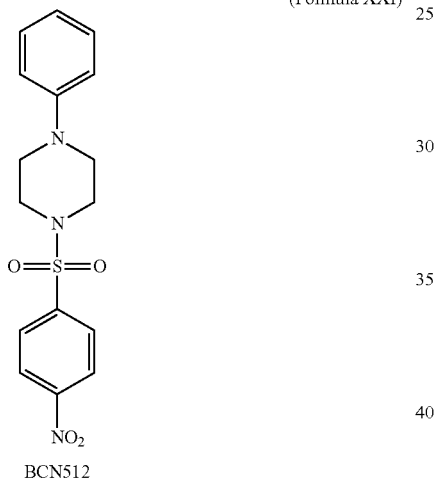
(Formula XXI)
BCN512
In some embodiments, the compound is an analog selected from Formula XXII-XVIII.
| BCN512 Analogs | Name |
|---|---|
| 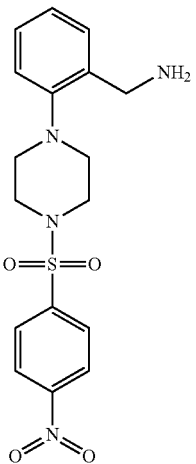 [SMILES: NCc1ccccc1N1CCN(S(=O)(=O)c2ccc([N+](=O)[O-])cc2)CC1] | Formula XXII (BCN52A1) |

| BCN512 Analogs | Name |
|---|---|
| 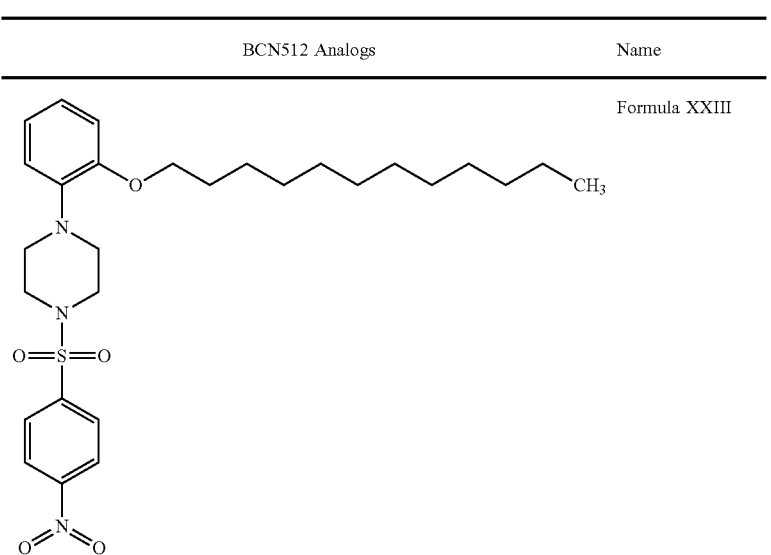 | Formula XXIII |
| 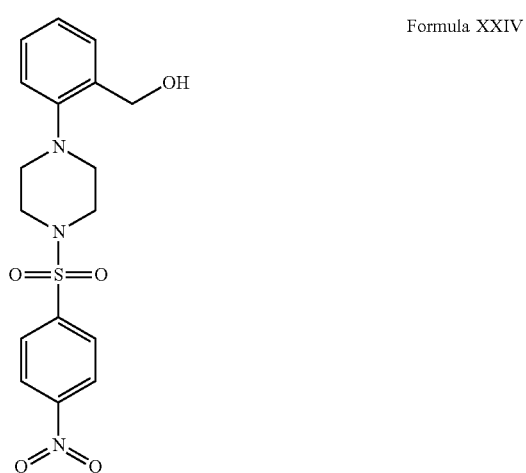 | Formula XXIV |
| 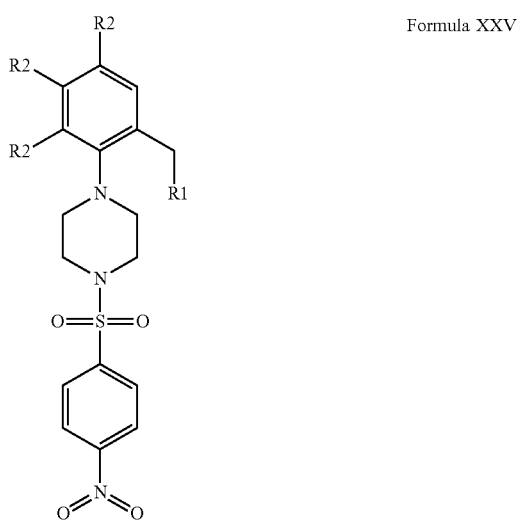 | Formula XXV |
$R_1$ = N, OH, $(CH_2)_n$—$CH_3$ or substituted or unsubstituted aryl;
$R_2$ = a halogen, N, OH, $CH_3$.

| BCN512 Analogs | Name |
|---|---|
| [Structure: 2-(piperazinyl)phenylacetic acid with 4-nitrobenzenesulfonyl group] | Formula XXVI |
| [Structure: 4-fluoro-2-(piperazinyl)benzylamine with 4-nitrobenzenesulfonyl group] | Formula XXVII |
| [Structure: 3-fluoro-2-(piperazinyl)phenyl-1-aminoethyl with 4-nitrobenzenesulfonyl group] | Formula XXVIII |

A compound of Formula I-XXVIII or analogs thereof disclosed herein can be prepared according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010. Exemplary methods of making the compound is provided in U.S. patent application Ser. No. 13/813,923 and U.S. patent application Ser. No. 14/889,719, herein incorporated by reference. The compounds also include pharmaceutically acceptable salts thereof, prodrugs thereof, hydrates thereof, solvates thereof and polymorphic crystals thereof. The compounds can be administered as pharmaceutical compositions.

Utility and Administration

The compounds described herein are useful in the methods of the invention and, while not bound by theory, are believed to exert their desirable effects in part through their ability to modulate Wnt-β catenin signaling. The Wnt pathway is involved in tissue development in embryos and tissue maintenance in adults. It controls a specific set of genes that that control cell growth, movement and cell survival. Chronic activation of these genes and aberrant activation of the Wnt pathway leads to uncontrolled cell growth and survival and can consequently drive cancer formation in a range of tissues including colon, skin, liver and ovary.

The Wnt signaling pathways are a group of signal transduction pathways which begin with proteins that pass signals into a cell through cell surface receptors. Aberrant activation of the Wnt pathway is implicated in human cancers, particularly those of the gastrointestinal (GI) tract. Inhibition of aberrant Wnt pathway activity in cancer cell lines can block their growth, presenting the possibility of new therapeutics.

Wnt ligands bind to LRP5/6 and Frizzled co-receptors present on epithelial crypt cells, leading to β-catenin stabilization and nuclear translocation where it binds to the nuclear transcription factor TCF4 to drive a gene-expression program that supports stem cell maintenance, proliferation and differentiation. Activation of Wnt/β-catenin signaling is also crucial for crypt regeneration following injury. Studies have demonstrated that Respondin 1 (RSPO1), an ISC growth factor and LGR5 receptor agonist, activates Wnt/βcatenin pathway to repair and regenerate the intestine following chemo-radiation-induced injury. DKK1, a negative regulator Wnt/β-catenin pathway, impairs the RSPO1-induced intestinal regeneration.

In the absence of a Wnt signal, the transcriptional activator β-catenin is actively degraded in the cell. Phosphorylated β-catenin is subsequently recognized and ubiquitinylated, resulting in its proteasomal degradation. Levels of free β-catenin consequently remain low, which allows the DNA-binding T-cell factor/lymphoid enhancer factor (Tcf/Lef) proteins to interact with transcriptional co-repressors to block target gene expression in the nucleus.

In addition to treating cancer, therapies that control Wnt/β-catenin signaling also potential in treating other ailments, including fibrosis, inflammatory conditions, bone growth, wound healing, osteoporosis, alopecia (i.e. hair loss), depression and viral infection. Accordingly, there is a need for compounds and methods that can inhibit and/or modulate Wnt/β-catenin signaling.

BCN057 and Analogs—Cancer Treatment and Therapies

Studies have demonstrated that the Wnt pathway is permanently activated in both inherited familial adenomatous polyposis and spontaneous forms of colon cancer. Chronic activation of the Wnt pathway in these cells drives their expansion into benign adenomas (also termed polyps), which frequently progress to invasive colon carcinoma. Approximately 90% of sporadic colon cancers show aberrant Wnt signaling activity, usually as the result of mutations in APC.

BCN057 is an anti-neoplastic small molecular that is effective in treating cancer, particularly pancreatic and gastrointestinal (GI) cancers. It can function with dual actions. It induces apoptosis in cancer cells. Second, it can promote growth and survival of epithelial cells. BCN057 is particularly effective against pancreatic and gastrointestinal (GI) cancers. BCN057 has demonstrated antineoplastic effects against "KRAS" cancers.

Use in Conjunction with Radio/Chemo Therapies

BCN057 is effective in treating cancer, particularly pancreatic and gastrointestinal (GI) cancers. In one aspect, disclosed herein, is a method of treating radiation induced gastrointestinal syndrome (RIGS) in a subject in need thereof, the method comprising the step of administering to the subject a therapeutically effective amount of a compound of BCN057 or an analog of BCN057. The analog can be one or more of the compounds of Formula II-XIX. BCN057 can mitigate RIGS and improve the therapeutic ratio for abdominal radiotherapy. Further, BCN057 mitigates radiation induced mucositis, including oral mucositis, GI mucositis, e.g., of the throat, stomach and intestines, enteritis and proctitis. Further, it can prevent and treat damage to epithelial tissue from radiation and chemotherapy. The compounds are also useful for treating or preventing these radiation syndromes associated with radiation therapy.

Combination Therapies

Combination therapy can be particularly effective with drugs that work by different mechanisms, thereby decreasing the likelihood that resistant cancer cells will develop. When drugs with different effects are combined, each drug can be used at its optimal dose, without intolerable side effects. BCN057 and a second medicament can be combined for therapeutic benefit. The second medicant can have a different mechanism. Alternatively, it can use the same mechanism as BCN057 for therapeutic benefit. The combination can act via a synergistic effect. Combination therapies can also include additional (e.g. a third, fourth, fifth, etc.) medicaments. BCN512 can be used in combination therapies in the same manner.

BCN512 and Analogs—SFRP Mediated Therapies

Many colon cancers carry silenced genes encoding members of the secreted Fzd-related protein (SFRP) or Wnt inhibitory factor (WIF) families, which act as natural brakes of the Wnt pathway. They can bind with Wnt ligands to block pathway activation at the cell surface. Without this inhibition, Wnt ligands produced by the cancer cells can activate the pathway at the membrane and amplify the aberrant Wnt signaling activity initiated by mutations in APC, β-catenin or Axin 2. This aberrant Wnt pathway activation can lead to cancer.

Wnt signaling begins when a Wnt protein binds to the N-terminal extra-cellular cysteine-rich domain of a Frizzled (Fzd) family receptor. When sfrp's are inhibited or at low levels, wnt ligand is able to bind to Fzd receptors and transduce wnt related gene expression. sfrp's also have anti-proliferative effects on vascular cells, in vitro and in vivo. In vascular cell cycle, they delay the G1 phase and entry into the S phase. In kidney development, sFRPS inhibit tubule formation and bud growth in metanephroi.

BCN512 can inhibit SFRP activity and disrupt its ability to bind wnt ligands. SFRPs act as negative regulators of wnt signaling by binding wnt ligand with a similar domain as the fzd receptor domain which wnt binds to when free to transduce canonical wnt signaling. This mechanism presents several therapeutic uses. BCN512 and its analogs can inhibit tissue fibrosis via inhibition SFRP's, including SRFP1. BCN512 and its analogs can activate bone growth through inhibition of SRFP's. BCN512 and its analogs can activate hair growth through inhibition of SRFP's.

If BCN512 and related structures inhibit the activity of SRFPs, BCN512 can allow more free Wnt ligand from epithelial cells. Free Wnt ligands are secreted and transported through exosomes. To determine the role of BCN512 in pulmonary epithelium derived Wnt release, exosomes were purified from organoid conditioned medium. Purified exosomes were tested for Wnt activity by the TOPFLASH assay. It was observed that exosomal Wnt activity is several folds higher in samples prepared from irradiated organoids treated with BCN512 compared to irradiated control. These results suggest that BCN512 also induces the endogenous Wnt release.

Additional studies have demonstrated that Wnt β-catenin signaling plays a critical role in restitution of bronchoepithelial stem cell pool. A previous study demonstrated that Wnt ligands were secreted and transported through exosome. It has been demonstrated that exosome derived from mice ex-vivo lung organoids contained Wnt ligands and demonstrated Wnt activity in response to BCN512 treated. Wnt activity has also been examined in exosomes derived from human lung organoids.

For the role of BCN512 in human pulmonary epithelium derived Wnt release, exosome were purified from organoid conditioned medium. Purified exosomes were tested for Wnt activity by TOPFLASH assay. It was observed that exosomal Wnt activity is several folds high in samples prepared from irradiated organoids (4-6 Gy) treated with BCN512 compared to irradiated control. These results suggest that BCN512 also induces the endogenous Wnt release from human pulmonary epithelium.

Inflammatory Diseases

BCN512 can be used to treat inflammatory diseases or conditions. Inflammatory skin diseases include, conditions associated with cell proliferation, such as psoriasis, eczema and dermatitis, (e.g., eczematous dermatitides, topic and seborrheic dermatitis, allergic or irritant contact dermatitis, eczema craquelee, photoallergic dermatitis, phototoxic dermatitis, phytophotodermatitis, radiation dermatitis, and stasis dermatitis). Other inflammatory skin diseases include, but are not limited to, scleroderma, ulcers and erosions resulting from trauma, burns, bullous disorders, or ischemia of the skin or mucous membranes, several forms of ichthyoses, epidermolysis bullosae, hypertrophic scars, keloids, cutaneous changes of intrinsic aging, photoaging, frictional blistering caused by mechanical shearing of the skin and cutaneous atrophy resulting from the topical use of corticosteroids. Additional inflammatory skin conditions include inflammation of mucous membranes, such as cheilitis, chapped lips, nasal irritation, mucositis and vulvovaginitis.

Inflammatory disorders of the endocrine system include, but are not limited to, autoimmune thyroiditis (Hashimoto's disease), Type I diabetes, and acute and chronic inflammation of the adrenal cortex. Inflammatory conditions of the cardiovascular system include, but are not limited to, coronary infarct damage, peripheral vascular disease, myocarditis, vasculitis, revascularization of stenosis, artherosclerosis, and vascular disease associated with Type II diabetes.

Inflammatory condition of the kidney include glomerulonephritis, interstitial nephritis, lupus nephritis, nephritis secondary to Wegener's disease, acute renal failure secondary to acute nephritis, Goodpasture's syndrome, post-obstructive syndrome, tubular ischemia, irritable bowel disorder, or inflammation induced colon malignancies.

Inflammatory conditions of the liver include hepatitis (arising from viral infection, autoimmune responses, drug treatments, toxins, environmental agents, or as a secondary consequence of a primary disorder), biliary atresia, primary biliary cirrhosis and primary sclerosing cholangitis.

Inflammatory conditions of the central nervous system include multiple sclerosis and neurodegenerative diseases such as Alzheimer's disease, Parkinson's disease, or dementia associated with HIV infection.

Other inflammatory conditions include periodontal disease, tissue necrosis in chronic inflammation, endotoxin shock, smooth muscle proliferation disorders, graft versus host disease, tissue damage following ischemia reperfusion injury, idiopathic pulmonary fibrosis, and tissue rejection following transplant surgery Treatment of Viral Infections Additional embodiments include the use of BCN057 and analogs of BCN057 for treatment of viral infections. A viral disease infection occurs when the body is invaded by pathogenic viruses, and infectious virus particles attach to and enter susceptible cells. The host immune response can mediate disease and excessive inflammation. The stimulation of the innate and adaptive immune system in response to viral infections destroys infected cells, which can lead to severe pathological consequences to the host (i.e. virus-induced immunopathology). Specifically, immunopathology is caused by the excessive release of antibodies, interferons and pro-inflammatory cytokines, activation of the complement system, or hyperactivity of cytotoxic T cells. Secretion of interferons and other cytokines can trigger cell damage, fever and flu-like symptoms. In severe cases of certain viral infections, as in avian H5N1 influenza in 2005, aberrant induction of the host immune response can elicit a flaring release of cytokines known as a cytokine storm.

Wnt signaling is important for the innate immune response to viruses. Pathogenic viruses suppress b-catenin downstream expression of critical genes to evade the first line of defense in the immune system. b-catenin is essential to the expression of IFN-α/β and the subsequent transcriptional activation of interferon-stimulated genes. IFN-β induces in an auto- and paracrine expression of antiviral-acting genes. Thus BCN057 and analogs of BCN057 can prevent pathological consequences such as virus-induced immunopathology.

Treatment of Depression

Additional embodiments include the use of BCN057 and analogs of BCN057 for treatment of depression. Wnt signaling is also important for treating depression. Since the 1950s Lithium carbonate and other salts have been used similarly to treat depression. Lithium works by inhibiting GSK3b in the wnt downstream signaling pathway and transcribing the b-catenin downstream genes.

Recent studies have demonstrated that altered Wnt signalling can play a role in the pathophysiology of mood disorders. β-catenin levels are reduced in the hippocampal CA3 and CA4 regions, and Wnt1 levels are increased in the hippocampal CA4 region of post-mortem schizophrenic brains. Because lithium inhibits glycogen synthase kinase3β (GSK3β), a component of the canonical Wnt pathway, the pathway has been proposed as a specific target in the treatment of bipolar disorders. Thus, BCN057 and analogs of BCN057 can be used to treat depression and mood disorders.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods and uses disclosed herein.

BCN057 for Treatment of Pancreatic Cancer

FIG. 1 depicts the Effects of 5-FU and BCN057 on the viability of pancreatic cancer cell lines. The Effects of 5-FU and BCN057 on the viability of pancreatic cancer cell lines were assessed by ATP Lite assay (Perkin Elmer). 50 uM 5Fu (5Fu, n=5), 50 uM 5Fu and 2, 5, 10, and 20 uM BCN057 (5Fu+BCN057, n=5) or 2, 5, 10.20 uM CN057 (CN057, n=5). Control cells (V, n=5) The Percent Phosphorylation was calculated by dividing the average value for each condition by the average value of the control cells (V) at each time point.

Figure 2A:
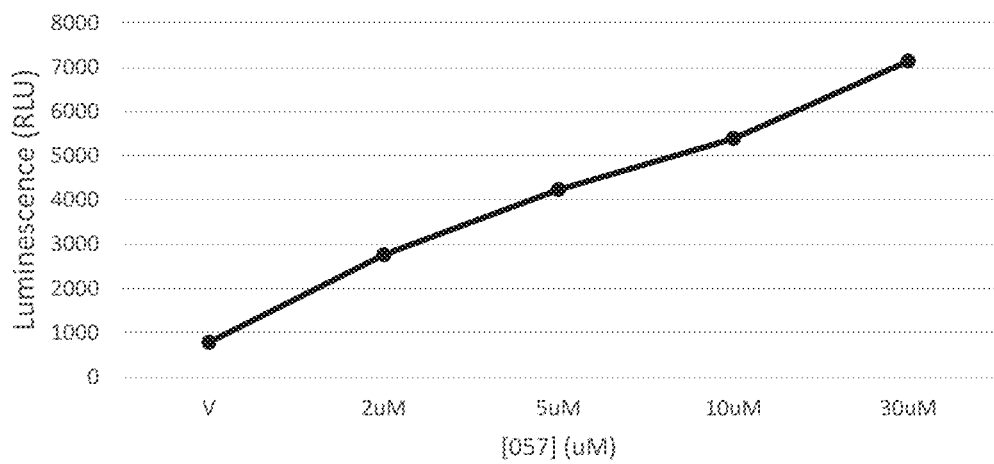
FIG. 2A shows the annexin V apoptosis and necrosis assay in Panc-1 cells in a dose dependent manner.
Figure 2B:
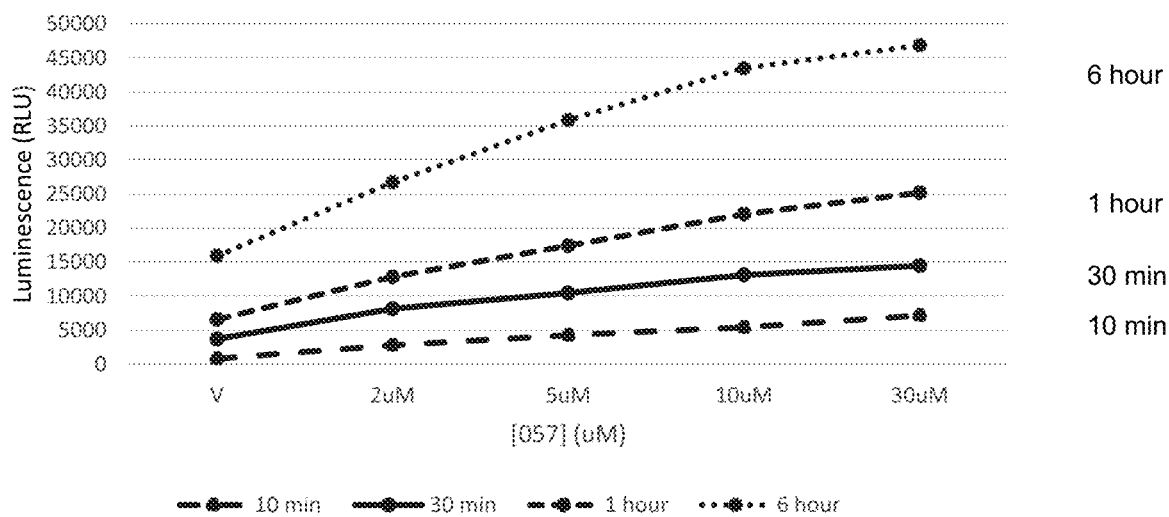
FIG. 2B shows the annexin V apoptosis and necrosis assay in Panc-1 cells over time.

FIGS. 2A and 2B depict the Annexin V Apoptosis and Necrosis Assay in Panc-1 cells. Panc-1 cells were exposed to serial dilutions of 057 in the presence or absence of the RealTime-Glo™ Annexin V Apoptosis and Necrosis Assay Reagent. The plate was incubated at 37° C./5% $CO_2$ and luminescence (Annexin V binding) was measured over a period of 6 hours. No change was observed in fluorescence over the same time period. Apoptosis appeared to increase with increasing concentrations of BCN057. FIG. 2A shows apoptosis as observed at 10 minutes (dose dependent). FIG. 2B shows apoptosis observed at 10 minutes, 30 minutes, 1 hour and 6 hours.

FIG. 3 depicts the Effects of 10 uM BCN057 on the viability of pancreatic cancer cell lines. The images show pancreatic cancer cell lines at time 0 (FIG. 3A), 15 minutes (FIG. 3B), 30 minutes (FIG. 3C), 60 minutes (FIG. 3D), 120 minutes (FIG. 3E) and 240 minutes (FIG. 3F). Morphological changes and apoptosis are particularly apparent at 240 minutes.

Figures 4A, 4B:
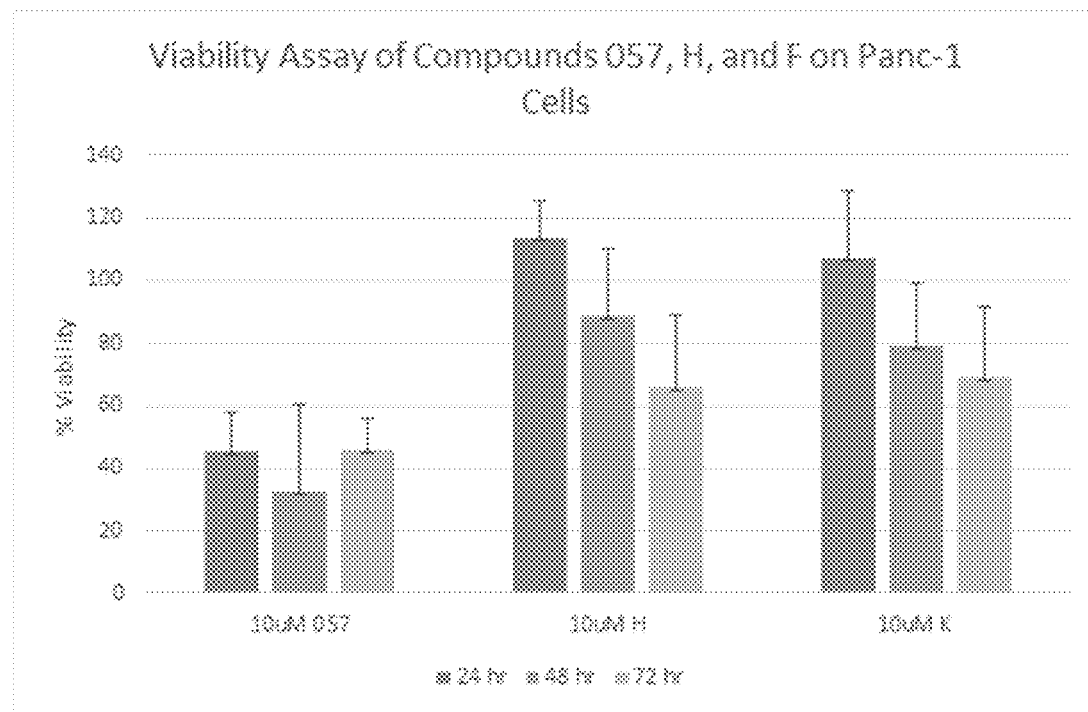
FIG. 4A is a graph of the results of a viability assay on pancreatic cells
FIG. 4B shows the data for each time point.
Figure 5A:
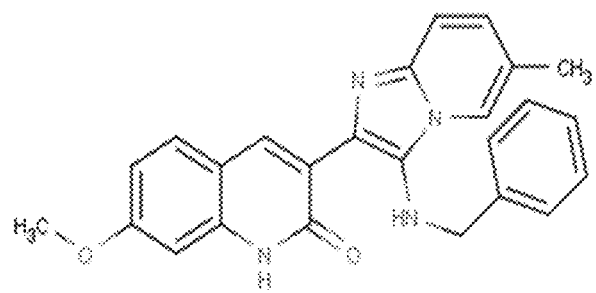
FIG. 5A depicts compound H.
Figure 5B:
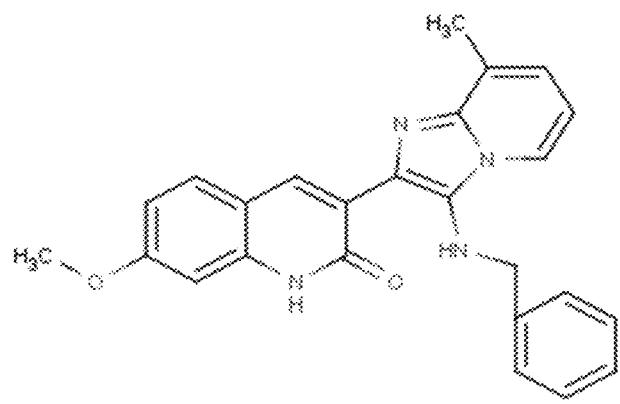
FIG. 5B depicts compound K.

FIGS. 4A and 4B show Compound H, Compound K and the results of a Viability Assay on Pancreatic Cells. The graph (FIG. 4A) shows the effects on viability of Panc-1 cancer cells in the presence of 10 uM of BCN057, compound H or K over 24, 48 and 72 hours. Each replicate (n=3) is displayed as a ratio of its vehicle control (a % of control). The numeric data is also included (FIG. 4B). FIG. 5A depicts Compound H and FIG. 5B depicts Compound K.

The results demonstrate that BCN057 has potent antineoplastic activity and inhibits the proliferation of the tumor cell line. This activity is complementary to chemotherapy such as 5-fluoro uracil.

The tests also demonstrate that BCN057 restores apoptosis in pancreatic cancer cells. Conversely, BCN057 allows for survival of stem cells and therefore prevents damage from chemotherapy induced damage to the epithelial tissue lining alimentary canal and digestive tract.

BCN512 for Treatment of Fibrosis

Fibrosis is generally defined as a pathological wound healing in which connective tissue replaces normal parenchymal tissue to the extent that it goes unchecked, leading to considerable tissue remodelling and the formation of permanent scar tissue. Pulmonary fibrosis is a lung disease that occurs when lung tissue becomes damaged and scarred. As explained in the specification (par. 095), every organ of the body can mount a repair response that generally results in a fibrotic lesion. Lung fibrosis as a result of chronic obstructive pulmonary disease and liver fibrosis because of hepatitis infection are two examples.

Figure 6:
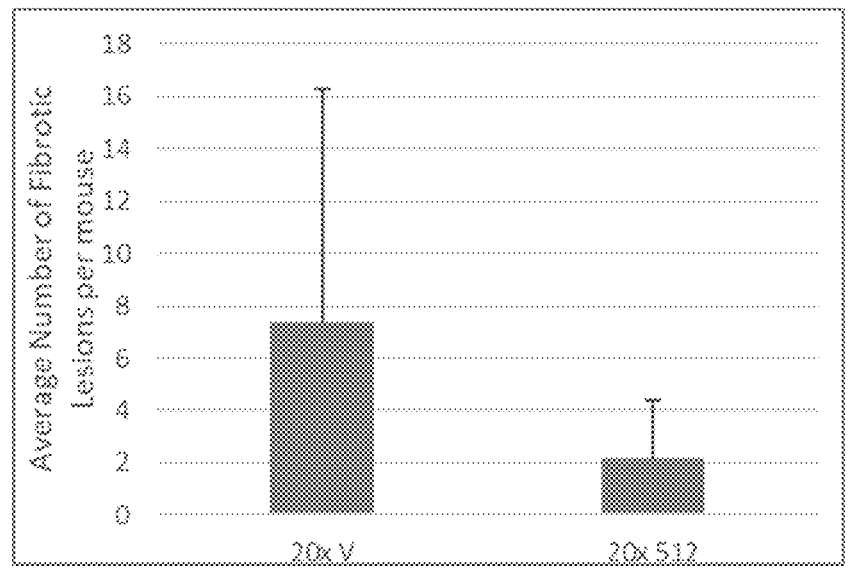
FIG. 6 is a graph that depicts fibrotic lesions in untreated lung tissue sections and sections treated with BCN512.

We propose that alveolar type II cells function as progenitor cells that repair the injured alveolar epithelium. Moreover, damaged epithelial cells also become major source of inflammatory cytokines. Therefore, mitigation of injury and progenitor/stem related re-building of the epithelium is critical to preventing or treating fibrosis FIG. 6 shows the number of fibrotic lesions in lung sections (untreated and treated with BCN512). There was a significant reduction in lung fibrosis in the BCN512 treated (20×512) vs. vehicle (20×V) upon final necropsy and histological analysis of lung in C57BL mice. Lesions were defined by local density with five mice per group assessed at day 180. This effect is observed with non-radiation induced stimuli such as LPS and cytotoxic drugs.

Transforming growth factor β (TGF-β) is a central mediator of fibrogenesis. TGF-β is upregulated and activated in fibrotic diseases and modulates fibroblast phenotype and function, inducing myofibroblast transdifferentiation while promoting matrix preservation. FIG. 7 shows the histopathology of lung sections stained for TGFβ in C57M Male mice receiving nothing (A), 14Gy thoracic radiation (B) or radiation and BCNB512 (C) and assessed on day 90 respectively. TGFβ is reduced when treated for the first 20 days post radiation with BCN512 at 5 mg/kg. Images D-F are cardiac muscle stains under the identical parameters above from the same animals. We noted significant reduction in staining for TGFβ. This shows TGFδ staining is lower in tissues from radiation damage when treated with the BCN512. We expect the same results using non-radiation induced stimuli including LPS and cytotoxic drugs.

These studies and observations are consistent with previous observations, specifically that WNT-catenin signaling promotes the self-renewal and differentiation of LGR5+ epithelial (lung, oral, intestinal) stem cells. Canonical WNT activity was measured in HEK293 cells having a TCF/LEF luciferase reporter construct. Luciferase activity was measured after 24 hours. BCN-512 treatment significantly increased luciferase activity in HEK293 cells compared with vehicle treated cells.

Modulation of macrophage function is also modulated. The absence of late effects in fibrosis from animals from long term radiation (observing from long term studies of the total body irradiation studies) along with the reduction of fibroblasts indicate these drugs are effective at preventing fibrosis and inflammation from both radiation or chemical means (LPS). Moreover, fibroblast proliferation is macrophage dependent and BCN512 inhibits this macrophage function. Together, the results described above demonstrate that the compound BCN512 can be administered to preserve stem cells and progenitor cells. This prevents connective tissue from replacing normal parenchymal tissue, thus preventing fibrosis.

Pharmaceutical Carriers and Administration

The present methods may prevent a disease or condition or one or more symptoms of a disease or condition. As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The compositions and methods of the present disclosure may be utilized to treat an individual in need thereof. In certain embodiments, the individual is a mammal such as a human, or a non-human mammal. When administered to an animal, such as a human, the composition or the compound is preferably administered or used as a pharmaceutical composition comprising, for example, a compound of the disclosure and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophilized for reconstitution, powder, solution, syrup, suppository, injection or the like. The composition can also be present in a transdermal delivery system, e.g., a skin patch.

A pharmaceutical composition disclosed herein may comprise a therapeutic compound in an amount sufficient to allow customary administration to an individual. In certain embodiments, a pharmaceutical composition disclosed herein may comprise, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In certain embodiments, a pharmaceutical composition disclosed herein may comprise, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may comprise in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still certain embodiments, a pharmaceutical composition disclosed herein may comprise in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

A pharmaceutical composition disclosed herein may comprise a solvent, emulsion or other diluent in an amount sufficient to dissolve a therapeutic compound disclosed herein. In certain embodiments, a pharmaceutical composition disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In certain embodiments, a pharmaceutical composition disclosed herein may comprise a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

The final concentration of a therapeutic compound disclosed herein in a pharmaceutical composition disclosed herein may be of any suitable concentration. In certain embodiments, the final concentration of a therapeutic compound in a pharmaceutical composition may be a therapeutically effective amount. In certain embodiments, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In certain embodiments, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In certain embodiments, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

In certain embodiments, a therapeutically effective amount of a therapeutic compound disclosed herein generally is in the range of about 0.001 mg/kg/day to about 100 mg/kg/day. In certain embodiments, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In certain embodiments, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, about 0.001 mg/kg/day to about 100 mg/kg/day, about 0.001 mg/kg/day to about 150 mg/kg/day, about 0.001 mg/kg/day to about 200 mg/kg/day, about 0.001 mg/kg/day to about 250 mg/kg/day, about 0.001 mg/kg/day to about 300 mg/kg/day, about 0.001 mg/kg/day to about 350 mg/kg/day, about 0.001 mg/kg/day to about 400 mg/kg/day, about 0.001 mg/kg/day to about 450 mg/kg/day, about 0.001 mg/kg/day to about 500 mg/kg/day, about 0.001 mg/kg/day to about 550 mg/kg/day, about 0.001 mg/kg/day to about 600 mg/kg/day, about 0.001 mg/kg/day to about 650 mg/kg/day, about 0.001 mg/kg/day to about 700 mg/kg/day, about 0.001 mg/kg/day to about 750 mg/kg/day, or about 0.001 mg/kg/day to about 800 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, about 0.01 mg/kg/day to about 100 mg/kg/day, about 0.01 mg/kg/day to about 150 mg/kg/day, about 0.01 mg/kg/day to about 200 mg/kg/day, about 0.01 mg/kg/day to about 250 mg/kg/day, about 0.01 mg/kg/day to about 300 mg/kg/day, about 0.01 mg/kg/day to about 350 mg/kg/day, about 0.01 mg/kg/day to about 400 mg/kg/day, about 0.01 mg/kg/day to about 450 mg/kg/day, about 0.01 mg/kg/day to about 500 mg/kg/day, about 0.01 mg/kg/day to about 550 mg/kg/day, about 0.01 mg/kg/day to about 600 mg/kg/day, about 0.01 mg/kg/day to about 650 mg/kg/day, about 0.01 mg/kg/day to about 700 mg/kg/day, about 0.01 mg/kg/day to about 750 mg/kg/day, or about 0.01 mg/kg/day to about 800 mg/kg/day. In certain embodiments, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, about 0.1 mg/kg/day to about 100 mg/kg/day, about 0.1 mg/kg/day to about 150 mg/kg/day, about 0.1 mg/kg/day to about 200 mg/kg/day, about 0.1 mg/kg/day to about 250 mg/kg/day, about 0.1 mg/kg/day to about 300 mg/kg/day, about 0.1 mg/kg/day to about 350 mg/kg/day, about 0.1 mg/kg/day to about 400 mg/kg/day, about 0.1 mg/kg/day to about 450 mg/kg/day, about 0.1 mg/kg/day to about 500 mg/kg/day, about 0.1 mg/kg/day to about 550 mg/kg/day, about 0.1 mg/kg/day to about 600 mg/kg/day, about 0.1 mg/kg/day to about 650 mg/kg/day, about 0.1 mg/kg/day to about 700 mg/kg/day, about 0.1 mg/kg/day to about 750 mg/kg/day, or about 0.1 mg/kg/day to about 800 mg/kg/day. In certain embodiments, an effective amount of a therapeutic compound disclosed herein may be in the range of, e.g., about 10 mg/kg/day to about 15 mg/kg/day, about 10 mg/kg/day to about 20 mg/kg/day, about 10 mg/kg/day to about 25 mg/kg/day, about 10 mg/kg/day to about 30 mg/kg/day, about 10 mg/kg/day to about 35 mg/kg/day, about 10 mg/kg/day to about 40 mg/kg/day, about 10 mg/kg/day to about 45 mg/kg/day, about 10 mg/kg/day to about 50 mg/kg/day, about 10 mg/kg/day to about 75 mg/kg/day, about 10 mg/kg/day to about 100 mg/kg/day, about 10 mg/kg/day to about 150 mg/kg/day, about 10 mg/kg/day to about 200 mg/kg/day, about 10 mg/kg/day to about 250 mg/kg/day, about 10 mg/kg/day to about 300 mg/kg/day, about 10 mg/kg/day to about 350 mg/kg/day, about 10 mg/kg/day to about 400 mg/kg/day, about 10 mg/kg/day to about 450 mg/kg/day, about 10 mg/kg/day to about 500 mg/kg/day, about 10 mg/kg/day to about 550 mg/kg/day, about 10 mg/kg/day to about 600 mg/kg/day, about 10 mg/kg/day to about 650 mg/kg/day, about 10 mg/kg/day to about 700 mg/kg/day, about 10 mg/kg/day to about 750 mg/kg/day, or about 10 mg/kg/day to about 800 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In certain embodiments, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In liquid and semi-solid formulations, a concentration of a therapeutic compound disclosed herein typically may be between about 50 mg/mL to about 1,000 mg/m L. In certain embodiments, a therapeutically effective amount of a therapeutic disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/m L.

The subject may be a human, rat, mouse, cat, dog, horse, sheep, cow, monkey, avian, or amphibian. In another embodiment, the cell is in vivo or in vitro. Typical subjects to which compounds of the disclosure may be administered will be mammals, particularly primates, especially humans. For veterinary applications, a wide variety of subjects will be suitable, e. g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

When administering to an organism, the compound may be administered by any suitable means. In some embodiments, the compounds or formulations are administered orally. In some embodiments, the compounds or formulations are administered by injection, e.g. subcutaneous, parenteral, or intravenous, injections.

In some embodiments the compound may be administered in combination with other potential mitigators. In a particular embodiment, the composition may be administered with growth factors, NSAIDs, chemotherapeutics, anti-inflammatories, antibiotics, Metformin (Glucophage, Glumetza, others), Sulfonylureas, Meglitinides, Thiazolidinediones, DPP-4 inhibitors, GLP-1 receptor agonists, SGLT2 inhibitors, and/or Insulin therapy, for the treatment of the above conditions. In one aspect, the growth factor can be G-CSF (aka filgrastim, NEUPOGEN®) or erythropoietin (aka EPOGEN®).

In other embodiments, the compositions may comprise an effective amount of a modulator and/or other pharmaceutically active agent in a physiologically-acceptable carrier. The carrier may take a wide variety of forms depending on the form of preparation desired for a particular route of administration. Suitable carriers and their formulation are described, for example, in Remington's Pharmaceutical Sciences by E. W. Martin. In some embodiments, the compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) or oral administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

In some embodiments, the compositions may be in a form suitable for administration by sterile injection. In one example, to prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). For parenteral formulations, the carrier will usually comprise sterile water, though other ingredients, for example, ingredients that aid solubility or for preservation, may be included. Injectable solutions may also be prepared in which case appropriate stabilizing agents may be employed. In one embodiment, the formulation includes at least one or more of methanesulfonic acid, povidone, benzyl alcohol, n-Methyl pyrrolidone, ethaonol, Poloxamer 188, lactic acid, Captisol (SBE-beta-CD), or Vitamin E, such as TPGS (d-alpha tocopheryl polyethylene glycol 1000 succinate).

Formulations suitable for parenteral administration usually comprise a sterile aqueous preparation of the compound, which may be isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or localized delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

In some embodiments, the compositions may be in a form suitable for oral administration. In compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. If desired, tablets may be sugar coated or enteric coated by standard techniques.

Compositions suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught. Formulations for oral use include tablets containing active ingredient(s) in a mixture with pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

A syrup can be made by adding the compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

In some embodiments, the composition can be in a form of nasal or other mucosal spray formulations (e.g. inhalable forms). These formulations can include purified aqueous solutions of the active compounds with preservative agents and isotonic agents. Such formulations can be adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

In some embodiments, the composition may be in a form suitable for rectal administration. These formulations may be presented as a suppository with a suitable carrier such as cocoa butter, hydrogenated fats, or hydrogenated fatty carboxylic acids.

In some embodiments, the composition may be in a form suitable for transdermal administration. These formulations may be prepared, for example, by incorporating the active compound in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, compositions of the disclosure may further include one or more accessory ingredient(s) selected from encapsulants, diluents, buffers, flavoring agents, binders, disintegrants, surface active agents, thickeners, lubricants, preservatives (including antioxidants), and the like.

In some embodiments, compositions may be formulated for immediate release, sustained release, delayed-onset release or any other release profile known to one skilled in the art. In some embodiments, the pharmaceutical composition may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target the site of a pathology. For some applications, controlled release formulations obviate the need for frequent dosing to sustain activity at a medically advantageous level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, microspheres, molecular complexes, nanoparticles, patches, and liposomes.

In some embodiments, the composition may comprise a "vectorized" form, such as by encapsulation of the compound in a liposome or other encapsulate medium, or by fixation of the compound, e.g., by covalent bonding, chelation, or associative coordination, on a suitable biomolecule, such as those selected from proteins, lipoproteins, glycoproteins, and polysaccharides.

In some embodiments, the composition can be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents. Alternatively, the compound may be incorporated in biocompatible carriers, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

In all embodiments, the compound or other active compounds may be present as pharmaceutically acceptable salts or other derivatives, such as ether derivatives, ester derivatives, acid derivatives, and aqueous solubility altering derivatives of the active compound. Derivatives include all individual enantiomers, diastereomers, racemates, and other isomers of the compounds. Derivatives also include all polymorphs and solvates, such as hydrates and those formed with organic solvents, of the compounds. Such isomers, polymorphs, and solvates may be prepared by methods known in the art, such as by regiospecific and/or enantioselective synthesis and resolution.

The ability to prepare salts depends on the acidity or basicity of the compounds. Suitable salts of the compounds include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic, cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Unless the context clearly indicates otherwise, compositions of all embodiments can comprise various pharmaceutically acceptable salts, or other derivatives described above.

The formulation and preparation of such compositions are well known to those skilled in the art of pharmaceutical formulation. Formulations can be found in Remington: The Science and Practice of Pharmacy.

The amount of the compound employed in the present disclosure to be used varies according to the condition, the patient/subject, and the extent of the condition.

The contents of all cited references (including literature references, issued patents, published patent applications) as cited throughout this application are hereby expressly incorporated by reference. The disclosure and the manner and process of making and using it, are described in such full, clear, concise and exact terms as to enable any person skilled in the art to which it pertains, to make and use the same.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

Dosing can be single dosage or cumulative (serial dosing), and can be readily determined by one skilled in the art. For instance, treatment may comprise a one-time administration of an effective dose of a pharmaceutical composition disclosed herein. Alternatively, treatment may comprise multiple administrations of an effective dose of a pharmaceutical composition carried out over a range of time periods, such as, e.g., once daily, twice daily, thrice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

In certain embodiments, the period of administration of a therapeutic compound is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In certain embodiments, a treatment regimen may comprise a period during which administration is stopped for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

The patient receiving this treatment is any animal in need, including primates, in particular humans, and other mammals such as equines, cattle, swine and sheep; and poultry and pets in general.

In other embodiments, the compounds described herein may be provided with the one or more additional therapeutic agents in a kit, e.g., as separate pharmaceutical formulations capable of being used together in a conjoint therapy as discussed herein, either together in a single container or in separate containers. In certain such embodiments, the kit may further include instructions for the conjoint administration of the pharmaceutical formulations, e.g., for treating or preventing any of the conditions discussed above.

Such combination products may employ compounds of this disclosure, or pharmaceutically acceptable salts thereof, within the dosage range described hereinbefore and the other pharmaceutically-active agent within its approved dosage range.

In some embodiments, the compound may be administered after the predicate event, such as after exposure to ionizing radiation, or after the initiation of exposure to radiation including accidental or therapeutic radiation. In one embodiment, the compound is administered immediately after the exposure. In another embodiment, the compound is administered within 12 hours of the exposure. In another embodiment, the compound is administered within 24 hours of the exposure. In another embodiment, the compound is administered at 24 hours after the exposure. In another embodiment, the compound is administered after 24 hours of exposure. In another embodiment, the compound is administered after 36 hours of exposure. In another embodiment, the compound is administered within 48 hours of exposure. In another embodiment, the compound is administered within 60 hours of exposure. In another embodiment, the compound is administered within 72 hours of the exposure. In another embodiment, the compound is administered within 84 hours of the exposure.

In a certain embodiment or a particular formulation Yel002/BCN057 was solubalized in aqueous solution at physiologically compatible pHs using 100 mM methanesulfonic acid (MSA)/10% povidone (PVP); 100 mM MSA/2% benzyl alcohol/2% N-methylpyrrolidone (NMP); and, 100 mM MSA/10% ethanol/1% Poloxamer 188. In a further aspect 100 mM lactic acid was added and also improved solubility for these mixtures. In yet another embodiment, a formulation comprising Yel002 and 30 wt % Captisol (SBE-beta-CD) and 100 mM MSA yielded excellent solubility at up to pH 4.1 or higher.

In another embodiment formulation for intravenous, subcutaneous and oral delivery of therapeutic levels of Yel002/BCN057 were developed comprising 30 wt % Captisol (SBE-beta-CD) and 100 mM MSA at pH 4.1 or higher (adjusted with 1.0 N NaOH).

The disclosure now being generally described, it will be more readily understood by reference to the following examples which are included merely for purposes of illustration of certain aspects and embodiments of the present disclosure and are not intended to limit the disclosure.

In other aspects of this embodiment, a molecule disclosed herein reduces the severity of a disease by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a fusion protein or chimeric molecule disclosed herein reduces the severity of a disease from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the present disclosure to be practiced otherwise than specifically described herein. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

All patents, patent publications, and other publications referenced and identified in the present specification are individually and expressly incorporated herein by reference in their entirety for the purpose of describing and disclosing, for example, the compositions and methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present disclosure, which is defined solely by the claims. Accordingly, the present disclosure is not limited to that precisely as shown and described.

What is claimed is:

1. A compound of Formula A,

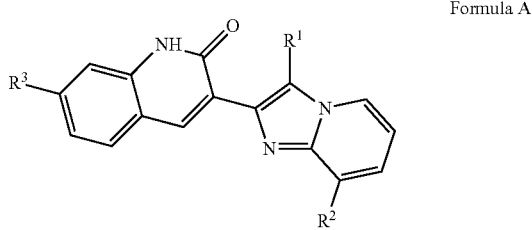

Formula A wherein $R^3$ is O—CH$_3$, $R^2$ is CH$_3$ or H and $R^1$ is one of:

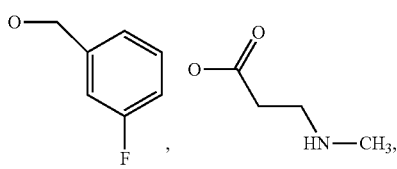

-continued

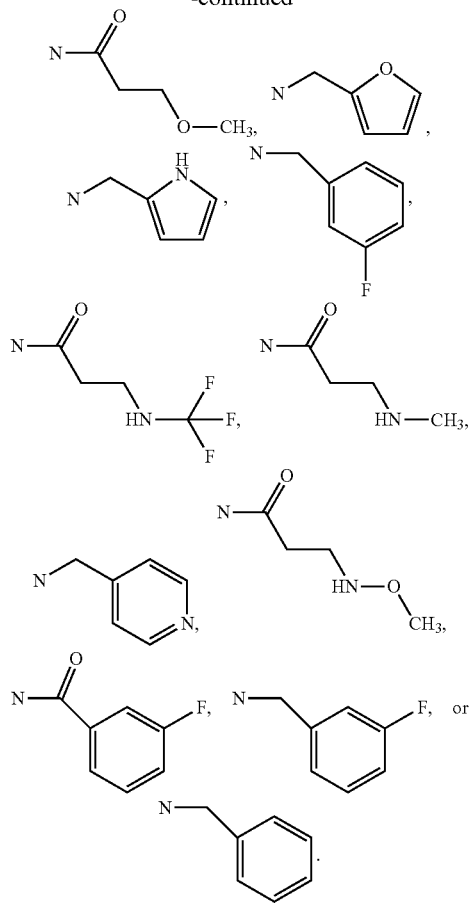

2. A method of treating cancer, a viral infection, or depression in a subject, comprising administering to the subject a therapeutically effective amount of a compound having the structure of Formula B:

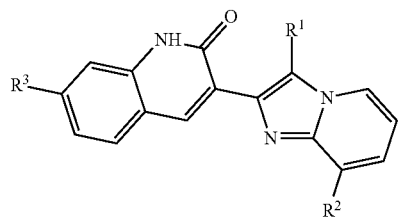

Formula B wherein:
$R^1$ is an alkyl, alkyl amine, or an ether;
$R^2$ is H or CH$_3$; and
$R^3$ is H or OH.

3. The method of claim 2, wherein the cancer is at least one of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, rectal cancer, skin cancer, blood cancer or testicular cancer.

4. The method of claim 2, wherein the method further comprises administering one or more additional medicaments to the subject.

5. The method of claim 2, wherein the method further comprises administration of chemotherapy or radiotherapy to the subject.

6. A method of treating a subject with one or more side effects of chemotherapy or radiotherapy, the method comprising administering to the subject a therapeutically effective amount of a compound of Formula B of claim 2.

7. A method of treating radiation induced damage to epithelial cells in a subject in need thereof, the method comprising the step of administering to the subject a therapeutically effective amount of a compound of Formula B of claim 2.

8. The method of claim 7, wherein the radiation induced damage to epithelial cells is identified as one or more of radiation-induced gastrointestinal syndrome (RIGS), radiation-induced mucositis, radiation-induced oral mucositis, radiation-induced proctitis or radiation-induced enteritis.

* * * * *